US012583863B2

(12) United States Patent
Parkinson et al.

(10) Patent No.: US 12,583,863 B2
(45) Date of Patent: Mar. 24, 2026

(54) SYNTHETICALLY MODIFIABLE ION CHANNELS

(71) Applicant: UNIVERSITY OF WYOMING, Laramie, WY (US)

(72) Inventors: Bruce Alan Parkinson, Laramie, WY (US); John Hoberg, Laramie, WY (US); Jordan Brophy, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 0 days.

(21) Appl. No.: 18/611,791

(22) Filed: Mar. 21, 2024

(65) Prior Publication Data

US 2024/0300967 A1 Sep. 12, 2024

Related U.S. Application Data

(63) Continuation of application No. 16/081,265, filed as application No. PCT/US2017/020000 on Feb. 28, 2017, now Pat. No. 11,976,078.

(60) Provisional application No. 62/321,867, filed on Apr. 13, 2016, provisional application No. 62/301,990, filed on Mar. 1, 2016.

(51) Int. Cl.
*C07D 487/22* (2006.01)
*B82B 3/00* (2006.01)

(52) U.S. Cl.
CPC .......... *C07D 487/22* (2013.01); *B82B 3/0014* (2013.01); *B82B 3/0042* (2013.01)

(58) Field of Classification Search
CPC .................................................... C07D 487/22
See application file for complete search history.

(56) References Cited

PUBLICATIONS

Kornmayer et al. (Organic Letters (2009), 11 (3), 725-728). Abstract.
Fu, C. et al., 2D Self-Assembly of Fused Oligothiophenes: Molecular Control of Morphology, ACS Nano, Aug. 7, J012, pp. 7973-7980, vol. 6, No. 9, © 2012 American Chemical Society; DOI: 10.1021/nn3025139.
Li, H. et al., Comparative studies on the electrochemical and optical properties of representative benzo[1,2-c;4,5-c0] bis[1,2,5]-thiadiazole, [1,2,5]-thiadiazolo[3,4-g]quinoxaline and pyrazino[2,3-g]quinoxaline derivatives, Journal of Materials Chemistry C, 2012, pp. 1745-1752, vol. 1, © 2013 The Royal Society of Chemistry; DOI: 10.1039/c2tc00212d.
Cardenas, L. et al., Synthesis and electronic structure of a two dimensional pl-conjugated polythiophene, Chemical Science, 2013, pp. 3263-3268, vol. 4, © 2013 The Royal Society of Chemistry; DOI: 10.1039/c3sc50800e.
Guo, J. et al., Conjugated organic framework with three-dimensionally ordered stable structure and delocalized pl clouds, Nature Communications, Nov. 13, 2013, pp. 1-8, vol. 4, No. 2736, © 2013 Macmillan Publishers Limited DOI: 10.1038/ncomms3736.
Medina, D.D. et al., Oriented Thin Films of a Benzodithiophene Covalent Organic Framework, ACS Nano, Feb. 24, 2014, pp. 4042-4052, vol. 8, No. 4, © 2014 American Chemical Society; DOI: 10.1021/nn5000223.
International Search Report dated Jun. 23, 2017 for International Application No. PCT/US2017/020000 filed Feb. 28, 2017.
Miyaura, N. et al., Palladium-Catalyzed Cross-Coupling Reactions of Organoboron Compounds, Chemical Reviews, 1995, pp. 2457-2483, vol. 95, Issue 7, © 1995 American Chemical Society; DOI: 10.1021/cr00039a007.
Mccusker, L.B. et al., Nomenclature of structural and compositional characteristics of ordered microporous and 2 mesoporous materials with inorganic hosts (IUPAC Recommendations 2001), Pure and Applied Chemistry, 2001, pp. 381-394, vol. 73, Issue 2, © 2001 IUPAC.
Guo, J. et al., Conjugated organic framework with three-dimensionally ordered stable structure and delocalized pl 3 louds, Nature Communications, Nov. 13, 2013, pp. 1-8, vol. 4, Article No. 2736, © 2013 Macmillan Publishers Limited; DOI: 10.1038/ncomms3736.
Joshi, R.K. et al., Precise and Ultrafast Molecular Sieving Through Graphene Oxide Membranes, Feb. 14, 2014, pp. 752-754, vol. 343, Issue 6172; DOI: 10.1126/science.1245711.
Algara-Siller, G. et al., Triazine-Based, Graphitic Carbon Nitride: a Two-Dimensional Semiconductor, Angewandte Chemie, May 14, 2014, pp. 7580-7585, vol. 126, Issue 29, © 2014 Wiley-VCH Verlag Gmbh & Co. KGaA, Weinheim; DOI: 10.1002/ange.201402191.
Fechler, N. et al., Eutectic Syntheses of Graphitic Carbon with High Pyrazinic Nitrogen Content, Advanced 6 Materials, Jul. 14, 2015, pp. 1287-1294, vol. 28, © 2015 Wiley-VCH Verlag Gmbh & Co. KGaA, Weinheim; DOI: 10.1002/adma.201501503.
Walker, M.I. et al., Measuring the proton selectivity of graphene membranes, Applied Physics Letters, Nov. 25, 2015, pp. 213104-1-213104-4, vol. 107, © 2015 AIP Publishing LLC; DOI: 10.1063/1.4936335.
Cheng, C. et al., Ion transport in complex layered graphene-based membranes with tuneable interlayer spacing, Science Advances, Feb. 12, 2016, pp. 1-9, vol. 2, Issue 2, e1501272, © 2016 The Authors; DOI: 10.1126/ , sciadv.1501272.

(Continued)

*Primary Examiner* — Bruck Kifle
(74) *Attorney, Agent, or Firm* — Patterson + Sheridan, LLP

(57) ABSTRACT

A new class of ordered functional nanoporous material (OFNMs) with a unique combination of electronic conductivity, gas transport ability, and ion transport properties are provided. The OFNM provided is highly ordered and contains nanometer scale pores lined with nitrogen atoms. The pores have dimensions of from 1.2 nm to 82 nm of longest linear extent across the pore. The functionality within the pore is controlled through selection of groups that extend into the pore. The degree of conjugated aromaticity is readily controlled to adjust the electrical conductivity properties of the resulting structure. By adjusting the groups external to the pore, three-dimensional structures are formed that are organic mimics of zeolites, metal organic frameworks (MOF), or perovskites.

8 Claims, 23 Drawing Sheets

(56) References Cited

PUBLICATIONS

Akbari, A. et al., Large-area graphene-based nanofiltration membranes by shear alignment of discotic nematic liquid crystals of graphene oxide, Nature Communications, Mar. 7, 2016, pp. 1-12, vol. 7, Article No. 10891; DOI: 10.1038/ncomms10891.
Office Action for U.S. Appl. No. 16/081,265 dated Apr. 21, 2023.
Final Office Action for U.S. Appl. No. 16/081,265 dated Dec. 7, 2023.
Office Action for U.S. Appl. No. 16/081,265 dated Aug. 29, 2022.

Dicyandiamide

Triazine-based carbon nitride

Heptazine-based carbon nitride

1

2

3

4

5

4 +
6
X = N or CH
7

SYNTHETICALLY MODIFIABLE ION CHANNELS

RELATED APPLICATIONS

This application is a continuation of co-pending U.S. patent application Ser. No. 16/081,265, filed on Feb. 28, 2017, which is a national stage entry of international PCT Patent Application No. PCT/US2017/020000, filed on Feb. 28, 2017, which claims the benefit of U.S. Provisional Patent Application No. 62/301,990, filed on Mar. 1, 2016, and the benefit of U.S. Provisional Patent Application No. 62/321,867, filed on Apr. 13, 2016, all of which are herein incorporated by reference in their entireties.

FIELD OF THE INVENTION

The present invention in general relates to materials and the synthesis of new families of Ordered Functional Nanoporous Materials (OFNMs); and in particular synthetic precursors and methods that yield to an entirely new class of ordered two-dimensional (2D) and three-dimensional (3D) nanoporous OFNMs with a unique combination of electronic conductivity, gas transport ability, supercapacitors, catalyst binding, and ion transport properties.

BACKGROUND OF THE INVENTION

The demonstration that single layers of graphite or graphene have extraordinary properties including specific optical activity, high carrier mobility, and high electrical and thermal conductivity, makes graphene a very promising candidate material for nanoelectronics. Graphene is a lattice of carbon atoms so thin that graphene is considered to be two-dimensional (2D) having $sp^2$-hydridized carbon atoms that afford planar conductivity. However, graphene is missing the typical electronic band gap that would make it a semiconductor. The electronic band structure of graphene resembles relativistic particle-antiparticle pairs. Graphene as a prototypical two dimensional (2D) material has initiated an explosion of interest in 2D materials, including the layered structure transition metal dichalcogenides with the prototypical $MoS_2$ structure, which are changed and sometimes enhanced properties at the single layer level. Substitutions of heteroatoms into the graphite structure can produce other 2D materials such as the isoelectronic, yet insulating, boron nitride that has improved strength and thermal characteristics relative to graphene. Simple substitution of nitrogen for carbon in graphene-like structures has resulted in several other ordered 2D OFNMs such as g-$C_3N_4$, $C_4N$, $CAN_3$ and the much more recent '$C_2N$ holey 2D crystal' or '$C_2N$-h2D'; however, most reports of nitrogen containing graphitic materials have no long range order or controllable pore size.

So-called porous covalent triazine-based framework (CTF) materials ($C_3N$) have been synthesized by polymerization of aromatic dinitriles in a $ZnCl_2$ molten salt at temperatures between 30° and 600° C. The prototypical CTF material used p-dicyanobenzene as a reagent to synthesize CTF1 is shown in prior art FIG. 1, and several other dinitriles have been employed to produce variations on this structure. Furthermore, various CTF frameworks have been made from p-dicyanopyrimidine and other aromatic ring systems such as 1,5-dicyanopyridine to form a CTF with the stoichiometry of $C_2N_3$ (prior art FIG. 2). These materials were mostly disordered, but calculations of the electronic properties of the ideal framework showed that these materials would be semiconducting.

There has also been considerable work on the $C_3N_4$ systems synthesized from a variety of routes, but most frequently from melamine polymerization. Most of these syntheses produced disordered materials until Algara-Siller et al. in 2014 made the first highly ordered material that could then be designated as g-$C_3N_4$, where g is for graphitic. (G. Algara-Siller et al., Angew. Chem. 2014, 126, 7580-7585). In the synthesis described by Algara-Siller et al., a molten salt was used with dicyandiamide heated to 600° C. for 60 hours in a LiBr/KBr eutectic sealed in a quartz ampule. Two different allotropes of g-$C_3N_4$, the triazine and heptazine based structures were produced from this reaction as seen in prior art FIG. 3. The triazine and heptazine based structures have semiconducting properties and have been examined for potential photovoltaic and photocatalytic properties.

The new g-$C_2N$ materials are of particular interest since they are made using a simple well-known condensation reaction between a ketone and amine at lower temperatures to form imine moieties, specifically hexaminobenzene and hexaketocyclohexane (HKC) in a highly exothermic reaction (−89. 7 kcal/mole from DFT) to form the g-$C_2N$, as shown in prior art FIG. 4. This material is semiconducting with a direct band gap of ~1.7 eV. It was also shown that these 2D crystals have an optical gap of 1.96 eV. The DPT calculations that have been performed revealed flat bands near the edges of the conduction and valence bands indicating a high level of delocalization of the x-states and implying high mobilities that were also measured in single layer FET devices. Interestingly, the valence band is doubly degenerate at the Γ-point. Such degeneracy can be removed by a pseudo-Jahn-Teller effect where electrons interact with phonons resulting in the buckling distortions of the 2D sheets. Annealed samples were also shown to be highly ordered and in a graphitic layered structure and were stable in argon to 900° C. and in air to 550° C. Field effect transistors (FETs) made from single flakes of g-$C_2N$ had exceptional properties with an average maximum on/off ratio between the maximum and minimum drain currents obtained from 50 devices of $4.6\times10^7$. The g-$C_2N$ material also has high electron and hole mobilities of 13.5 $cm^2$/V-s and 20.6 $cm^2$/V-s respectively on what is likely a rather defective material.

Recently, Guo et al. have reported a conjugated organic framework with a delocalized pi-electronic structure, yet one that lacks additional reactive moieties. Guo, J. et al.; Conjugated organic framework with three-dimensionally ordered stable structure and delocalized π clouds, *Nature Communications* 4, Article number: 2736 (2013) doi: 10.1038/ncomms3736.

However, it has been found that the performance of g-$C_2N$ material may be improved by modification of the reaction conditions to form larger crystallites with more order. Therefore, there exists a need for a process and materials formed thereof for improved nitrogen containing graphitic materials.

SUMMARY OF THE INVENTION

A new class of Ordered Functional Nanoporous Materials (OFNMs); with a unique combination of electronic conductivity, gas transport ability, and ion transport properties are provided. The OFNM provided is highly ordered and contains nanometer scale pores lined with nitrogen atoms and prepared from simple organic reagents at low temperatures compared to solid-state synthesis. The pores having dimensions of from 1.2 nm to 82 nm of longest linear extent across the pore. The functionality within the pore is controlled through selection of groups that extend into the pore. The degree of conjugated aromaticity is readily controlled to adjust the electrical conductivity properties of the resulting structure. By adjusting the groups external to the pore, three-dimensional structures are formed that are organic mimics of zeolites, metal organic frameworks (MOF) or covalent organic frameworks (COF).

A nitrogen containing graphitic material have at least one nanopore is provided that is crystalline and based on a basic building unit of the structure (I)—(IV):

a condensate of at least like three basic building blocks (BBUs) having the structure:

(I)

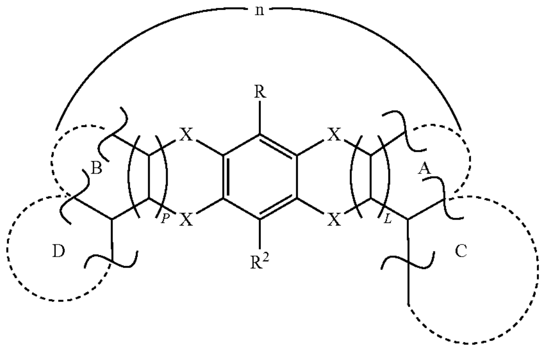

where R and $R^2$ are each independently in each occurrence H, Cl, Br, I, $C_4H_4S$ (thiophenyl), $SO_3$—, $CO_2^-$, C≡CH, CH≡$CH_2$, $NH_3^+$, OH, C≡N, $C_1$-$C_4$ alkyl, $(CH_2)_x$CH≡$CH_2$, or $(CH_2)_y$CH≡CH$(CH_2)_z$ where x or (y+z) is an integer of 0 to 4 inclusive, $(CH_2)_j$CH≡CH, or $(CH_2)_k$CH≡C$(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, thiol, amine (primary, secondary, tertiary or ammonium), hydroxyl, carboxyl, carbonyl, sulfonyl, or $C_2$-$C_4$ alkenyl; subject to the proviso that R and $R^2$ are not both alkyls in general and specifically not t-butyl; X is independently in each occurrence an $sp^2$-hybridized carbon atom-H, methylene, N—H or a nitrogen atom, with the proviso that at least one X is the N—H or the nitrogen atom; P and L are each independently the structure as shown absent the parentheticals (equal to 1) or includes an additional —$(CH_2\acute{C}H\acute{C}HCH_2)_{1-3}$— or —$(CH\acute{C}\acute{C}CH)_{1-3}$ that forms an additional 1 or 2 or 3 6-membered aliphatic or aromatic rings in each occurrence resulting in tetracyclic to a enneacyclic central structure in structure (I) bounded by rings A and B, Ć denotes an $sp^3$- or $sp^2$-hybridzed carbon with a bond fragment extending to complete bond to ring A or ring B for P and M, respectively, A and B are independently in each occurrence a three carbon fragment that forms a 6-membered ring that joins to form A-B continuous structures between adjacent basic building blocks (BBUs); n is an integer of between 3 and 12, C and D are independently in each occurrence —$(CHRCR^3C\ R^4CH_2)_{1-3}$— or —$(CHCR^3CR^4CR)_{1-3}$ that forms an additional 6-membered aliphatic or aromatic ring of which two carbons are common between rings A-C and C-D,

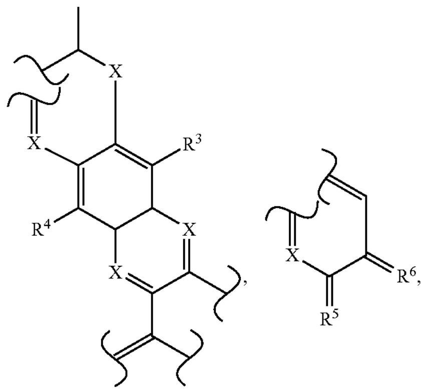

or

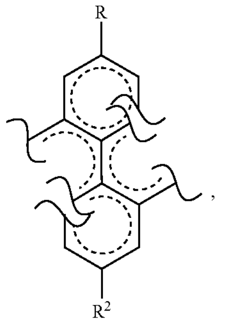

in which $R^3$ and $R^4$ are each independently in each occurrence H, Cl, Br, I, $C_4H_4S$ (thiophenyl), $SO_3^-$, $CO_2^-$, C≡CH, CH—$CH_2$, $NH_3^+$, OH, C═N, $C_1$-$C_4$ alkyl, $(CH_2)_x$CH≡$CH_2$, or $(CH_2)_y$CH≡CH$(CH_2)_z$ where x or (y+z) is an integer of 0 to 4 inclusive, $(CH_2)_j$CH≡CH, or $(CH_2)_k$CH≡C$(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, thiol, amine, hydroxyl, carboxyl, sulfonyl, or $C_2$-$C_4$ alkenyl; $R^5$ and $R^6$ are each independently in each occurrence O or NH; and any partial bonds depicted are completed by joining to complementary portions of other rings C or D to form a composite pore structure; or (II)

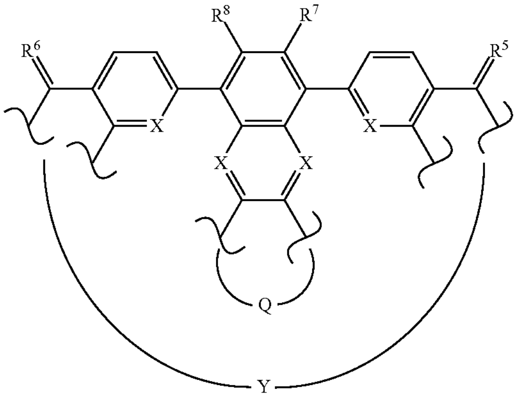

where $R^7$ and $R^8$ are independently in each occurrence H, Cl, Br, I, $C_4H_4S$ (thiophenyl), $SO_3^-$, $CO_2^-$,C≡CH, CH—$CH_2$, $NH_3^+$, OH, C≡N, $C_1$- $C_4$ alkyl, $(CH_2)_xCH{\equiv}CH_2$, or $(CH_2)_yCH{\equiv}CH(CH_2)_z$ where x or (y+z) is an integer of 0 to 4 inclusive, $(CH_2)_jCH{\equiv}CH$, or $(CH_2)_kCH{\equiv}C(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, thiol, amine (primary, secondary, tertiary or ammonium), hydroxyl, carboxyl, carbonyl, sulfonyl, or $C_2$-$C_4$ alkenyl; X is independently in each occurrence an $sp^2$-hybridized carbon atom-H, methylene, N—H or a nitrogen atom with the proviso that at least one X is the N—H or the nitrogen atom, Q is an integer value of 3 to form a 6-membered ring; Y is an integer value of 3 to form trifold symmetry pores of bounded by 13 total carbon or nitrogen atoms; $R^5$, and $R^6$ have the aforementioned definitions; or (III)

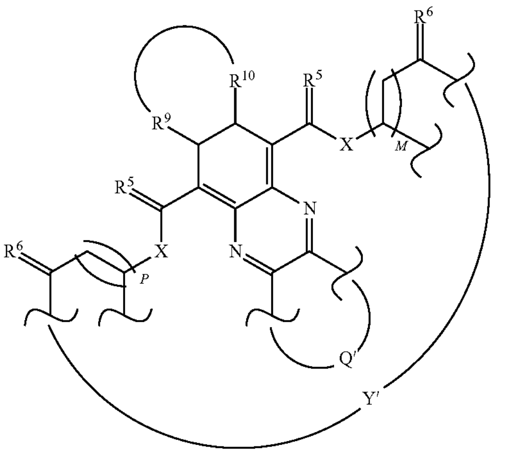

where $R^9$ and $R^{10}$ together are —N=C($R^{11}$) C($R^{12}$)=N—, —N—S—N—, —N—O—N—, and form a five-, or six-membered ring; $R^{11}$ and $R^{12}$ are independently in each occurrence R and $R^2$, respectively or combine to form polycyclic of triphenyl-2, 3, 6, 7 tetraone; P and M are each independently the structure as shown absent the parentheticals or includes an additional $—(CH_2\acute{C}H\acute{C}HCH_2)_{1\text{-}3}—$ or $—(CH\acute{C}\acute{C}CH)_{1\text{-}3}$ that forms an additional 1 or 2 or 3 6-membered aliphatic or aromatic rings in each occurrence resulting in tetracyclic to a enneacyclic central structure in structure (III), $\acute{C}$ denotes an $sp^3$- or $sp^2$-hybridzed carbon with a bond fragment extending to complete a pore through repetition of unit structure (III); Q' is an integer value of 3 to form a 6-membered ring; Y' is an integer value of 3 forming a pore inclusive of the clefts between P and Q', and between M and Q'; $R^5$, $R^6$, P and M have the aforementioned definitions; or (IV)

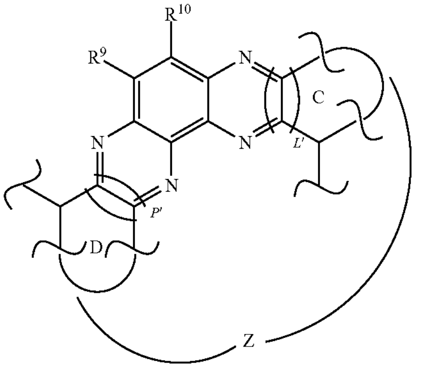

where P' and L' are each independently the structure as shown absent the parentheticals or includes an additional $—(CH_2\acute{C}H\acute{C}HCH_2)_{1\text{-}3}—$ or $—(CH\acute{C}\acute{C}CH)_{1\text{-}3}$ that forms an additional 1 or 2 or 3 6-membered aliphatic or aromatic rings in each occurrence; Z is an integer value of from 3 to 6; and $R^9$, $R^{10}$, C and D have the aforementioned definitions.

BRIEF DESCRIPTION OF THE DRAWINGS

The present invention is further detailed with respect to the following drawings. These figures are not intended to limit the scope of the present invention but rather illustrate certain attributes thereof.

DETAILED DESCRIPTION OF THE INVENTION

Figure 1:
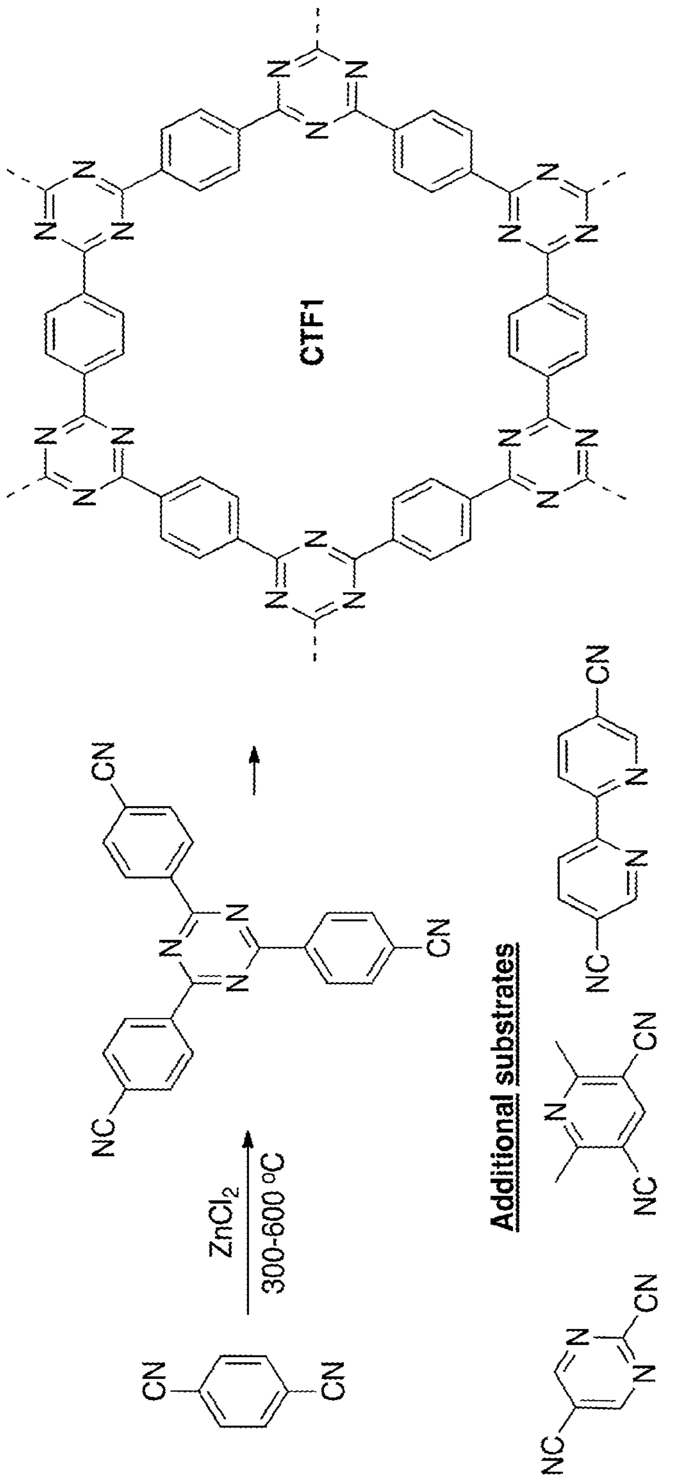
FIG. 1 illustrates a prior art synthesis of CTF1 with the use of a prototypical material p-dicyanobenzene.
Figure 2:
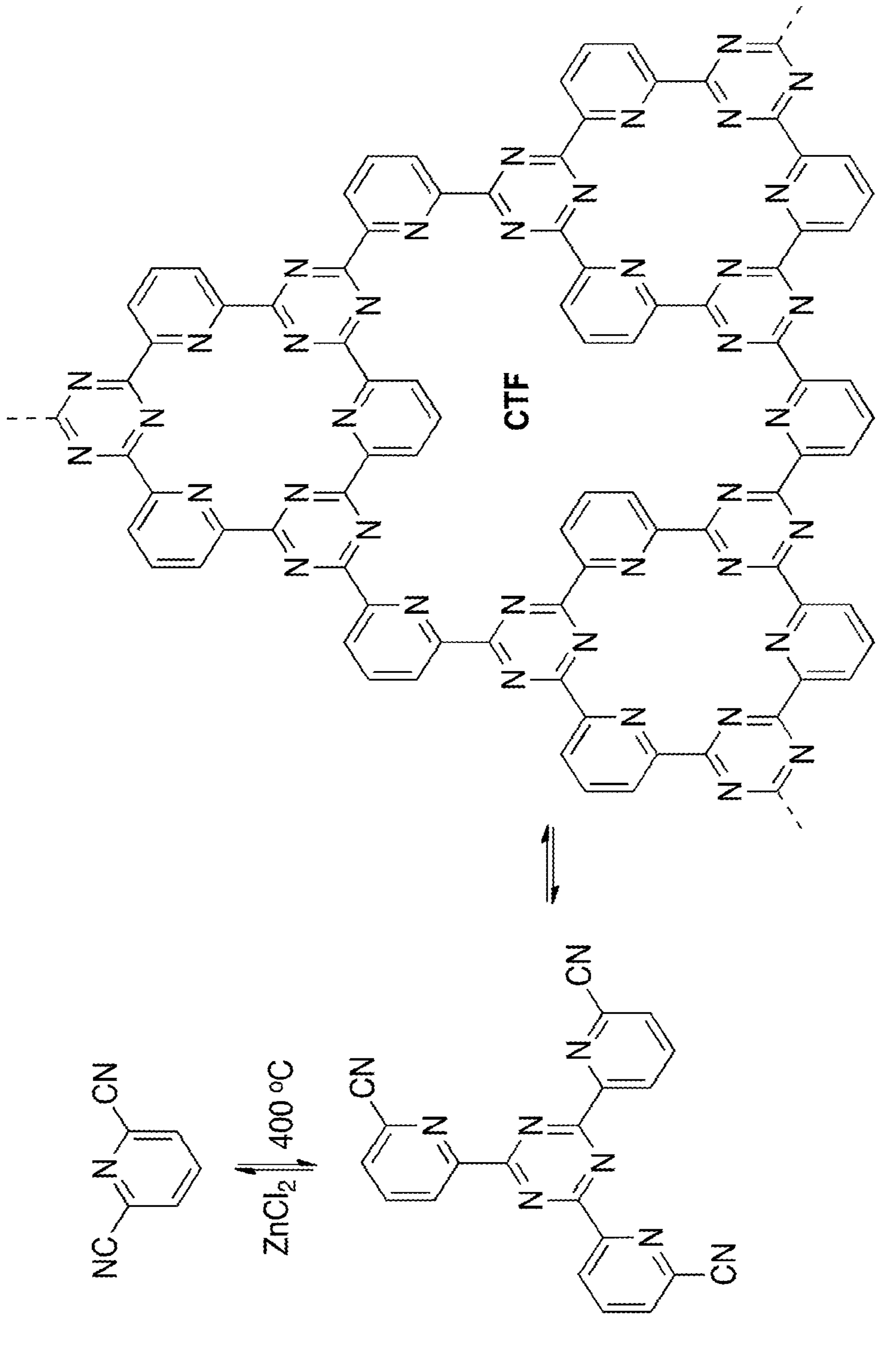
FIG. 2 illustrates a prior art synthesis of a CTF with 1,5 dicyanopyridine to form a CTF with the stoichiometry of $C_2N_3$.
Figure 3:
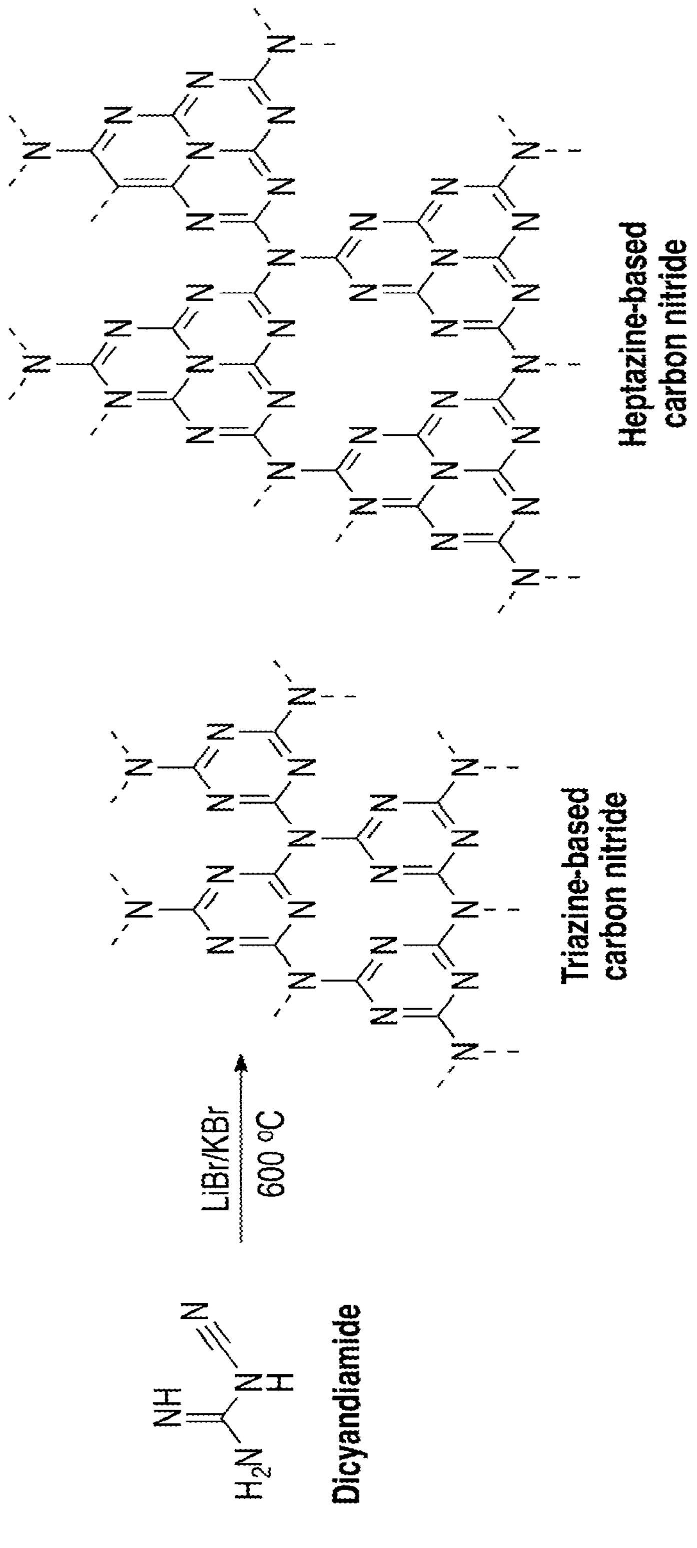
FIG. 3 illustrates a prior art reaction that results in two different allotropes of g-$C_3N_4$, triazine and heptazine based structures.

The present invention has utility in providing a method to synthesize new families of Ordered Functional Nanoporous Materials (OFNMs) that can be manipulated with targeted organic synthesis. As used herein, OFNMs are synonymously referred to herein as two-dimension OFNMs or nitrogen containing graphitic materials (NCGMs). The OFNMs so produced represent a range of new functional materials applicable to: selective ion transport membranes, selective gas transport membranes, battery electrodes, electrolyzer electrodes, fuel cell electrodes, desalinization systems, bipolar membranes, field-effect transistors, sensors, filters, supercapacitors and chemical and electrochemical catalysis. An inventive reaction scheme provides for self-assembly of inventive materials with long-range order.

The ability to incorporate large amounts of charge, nanostructured on the scale of compact double layer thickness in concentrated electrolytes and electronically conductive makes the inventive materials well-suited for supercapacitors. The inventive materials offer considerable advantages over conventional disordered nanostructured carbon in this context.

Inventive materials containing nitrogen containing ring structures afford the ability to quaternize the pore nitrogens to add functionality and thereby the addition of positive charges to a nanopore.

The ability to control both nanopore size and charge also make the inventive materials amenable to usage as gas separation. Illustrative gas separations to which the inventive material are applied illustratively include $O_2$ from $N_2$ separation, He separation, and $H_2$ separation.

A "basic building block" (BBU) and a "composite building unit" (CBU) as used herein are defined as detailed in L. B. McClusker et al., Pure Appl. Chem., Vol. 73, No. 2, pp. 381-394, 2001. It is appreciated that CBUs according to the present invention can be ordered not only in two- and three-dimensions, but also have fractal ordering defined by a non-integer ordering having a value of between 2 and 3.

As depicted herein a covalent chemical bond depicted at half-length and intersected by a tilde-like line denotes a bond dissected by repeat unit border of a BBU according to the present invention. A complementary single or double bond completes the bond with an a specific moiety, unless otherwise detailed herein.

The term "nanopore" is used herein synonymously with pore and intended to define a central void with a longest linear dimension in the plane of an inventive OFNM ranging from 1.2 nanometers (nm) to upwards of 82 nm.

As used herein, an aromatic, a heteroaromatic, an amino acid, a glycol, a sugar, are defined as each having a molecular weight of less than or equal 300 atomic mass units.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Embodiments of the invention provide an entirely new class of ordered two-dimensional (2D) Ordered Functional Nanoporous Materials (OFNMs) with a unique combination of electronic conductivity, gas transport ability, and ion transport properties. The inventive new materials provided by embodiments of the invention are in some inventive embodiments based on the synthesis of g-$C_2N$ (g is for graphitic), and are characterized by highly ordered OFNM containing nanometer scale pores lined with nitrogen atoms and prepared from simple organic reagents at low temperatures. The pores having dimensions of from 1.2 nm to 82 nm of longest linear extent across the pore and are synonymously referred to herein as nanopores. It is appreciated that the functionality within the pore is readily controlled through selection of groups such as R, $R^2$, $R^3$, and $R^4$ in the following structures, in addition to control over pore size and functionality, according to the present invention, the degree of conjugated aromaticity is readily controlled to control the electrical conductivity properties of the resulting structure. It is further appreciated that by bonding the external variable functionalities $R^7$, $R^8$, $R^9$, and $R^{10}$ in the following structures of a first CBU to those of a second CBU via a polymeric or oligomeric molecule, that three dimensional structures are formed that are organic mimics of zeolites, metal organic frameworks (MOP), or perovskites.

A novel syntheses method is provided that produces ordered 2D and 3D OFNMs containing chemically modifiable and controllable sized nanopores with many functional groups including charged carboxylates, sulfonates, and protonated amines that will be selective for binding and transporting either cations or anions of any desired size. Specific binding sites for binding catalytic transition or rare earth metals may also be incorporated into the materials for binding and electrocatalysis of specific chemical substrates.

The entirely new configurations and properties associated with the inventive OFNMs formed in embodiments of the invention have a myriad of applications that illustratively include size selective ion transporting membranes for fuel cells, redox flow batteries, electrolyzers, filtration, and desalinization systems. The inventive OFNMs are ideal for battery electrodes due to their rigidity, stability, and electronic conductivity, which have almost no dimensional changes upon charge/discharge cycles, and can be designed with nanopores to be selective for transporting and storing a particular high energy redox species such as Li, Na, Al or Ca. Since the inventive OFNMs are prepared to selectively bind and transport anions, and are also useful as membranes for conventional transition metal containing redox flow batteries. Stacking layers of anion and cation specific materials also enables use of the inventive OFNMs in bipolar membranes for many different applications. The ability to also incorporate electrocatalytic metals into specifically designed binding sites within the same material is a major advancement in fuel cell and electrolyzer designs by incorporating electronic conduction, ion transport, electrocatalysis, and gas transport within the same material.

In contrast to the prior art single layers of graphite, graphene oxide, or transition metal dichalcogenides that can only be modified by creating defects in which it is difficult to control both the number and exact sizes of the nanopores. Embodiments of the inventive OFNMs provide entire new families of two-dimensional materials that can rationally be designed for properties that graphene lacks. Embodiments of the inventive materials are unlike previously made nitrogen containing 2D structures, and are made so called bottom-up with routine organic synthesis methods making them amenable to the application of the vast knowledge base for targeted organic synthesis. The inventive synthetic formulations allow for variation of the delocalization within the aromatic framework, the number and position of the heteroatoms, the size of the nanopores in the structures, including multiple sized nanopores, and include chemical functionality within the nanopores. The electronic structure of the materials may be influenced by both the 2D aromatic heteroatom framework and by the electronic withdrawing or donating ability of the functional groups added in the nanopores. The functionality within the nanopores allows for targeting the materials for specific functions and applications. For instance, designing and fabricating ion or molecule specific membranes is one of the biggest challenges for both increasing the efficiency and lowering the cost of many important future technologies including fuel cells, batteries, desalination, gas separation and redox flow batteries. In addition, building ion/molecule specific transport and binding into the bulk properties of an electronic material enhance the specificity, lifetime and sensitivity of sensors based on field effect transistors made with inventive semiconducting materials disclosed herein. The variable band gaps and ability to layer 2D materials results in new heterojunction solar cell concepts based on p-n junctions from layering these materials with other layered materials, such as graphene for transparent conductive contacts, where the lattice matching needed in 3D heterojunction solar cells would not be necessary with only van-der Waals contacts between the layers without dangling bonds to induce traps state and recombination centers.

Unlike the previously described ordered carbon nitride syntheses that use molten salts reacted under extreme temperature in shock tubes, embodiments of the inventive reaction which are detailed below, are amenable to optimization of the solvent and reaction conditions common in organic synthesis. Furthermore, these new materials are amenable to targeted organic synthesis to produce new families of functional materials with both larger and more varied pores or nanopores and with functional groups within the nanopores. The inventive NGCM materials are unique in being the only electronically conductive materials, save for other than conductive polymers, which have bulk structure and properties amenable to modification by targeted organic synthesis. In contrast to conductive polymers, that can also be rationally synthesized and are difficult to control in applications due the one dimensional (1D) structures that result in disorder in chain lengths, and contain defects such as kinks in chains as well as different crystalline and amorphous phases and even voids in the solids, the inventive OFNMs are more ordered due to the 2D nature and thus allowing fewer degrees of freedom that facilitate an ordered fashion in the solid state.

A first inventive basic building block (I) is provided:

(I)

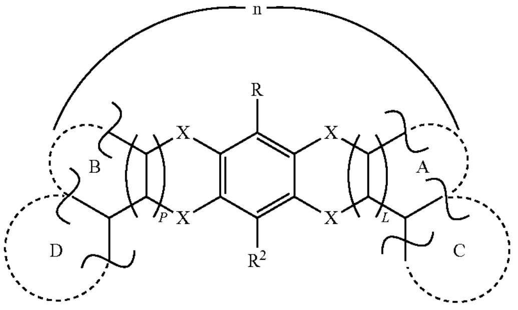

where R and $R^2$ are each independently in each occurrence H, Cl, Br, I, $C_4H_4S$ (thiophenyl), $SO_3^-$, $CO_2^-$, C≡CH, CH≡$CH_2$, $NH_3^+$, OH, C≡N, $C_1$-$C_4$ alkyl, $(CH_2)_xCH{\equiv}CH_2$, or $(CH_2)_yCH{\equiv}CH(CH_2)_z$ where x or (y+z) is an integer of 0 to 4 inclusive, $(CH_2)_jCH{\equiv}CH$, or $(CH_2)_kCH{\equiv}C(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, thiol, amine (primary, secondary, tertiary or ammonium), hydroxyl, carboxyl, carbonyl, sulfonyl, or $C_2$-$C_4$ alkenyl; it is appreciated that the aforementioned alkyls, alkenyls, or alkynyls are each linear, branched or cyclic, subject to the proviso that R and R2 are not both alkyls in general and specifically not t-butyl; X is independently in each occurrence an sp2-hybridized carbon atom-H, methylene, N—H or a nitrogen atom, with the proviso that at least one X is the N—H or the nitrogen atom; P and L are each independently the structure as shown absent the parentheticals (equal to 1) or includes an additional $-(CH_2CHCHCH_2)_{1-3}-$ or $-(CHCCCH)_{1-3}$ that forms an additional 1 or 2 or 3 6-membered aliphatic or aromatic rings in each occurrence resulting in tetracyclic to a enneacyclic central structure in structure (I) bounded by rings A and B, C denotes an $sp^3$- or $sp^2$-hybridzed carbon with a bond fragment extending to complete bond to ring A or ring B for P and M, respectively, A and B are independently in each occurrence a three carbon fragment that forms a 6-membered ring that joins to form A-B continuous structures between adjacent basic building blocks (BBUs), it is appreciated that rings A or B can in each occurrence be either aliphatic or aromatic, n is an integer of between 3 and 12 and denotes the numbers of BBUs that define the outer dimensions of a central nanopore, rings C and D represent exterior functionality created exterior to the nanopore, this functionality is exploited to create complex multi-pore planar structures, chemical bonds to disparate molecules, form composite building units in 3 dimensions, or combinations thereof, C and D are independently in each occurrence-$(CHRCR^3CR^4CH_2)_{1-3}$— or —$(CHCR^3CR^4CR)_{1-3}$ that forms an additional 6-membered aliphatic or aromatic ring of which two carbons are common between rings A-C and C-D,

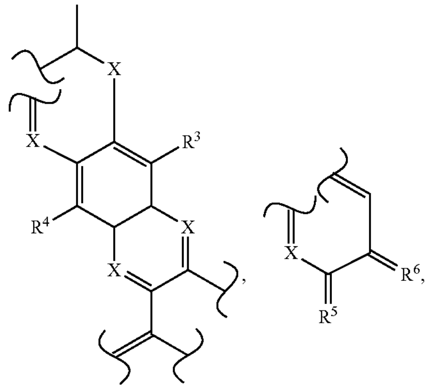

or

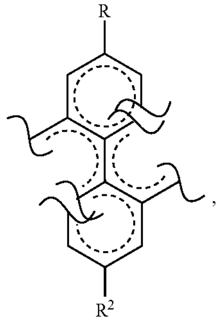

, in which $R^3$ and $R^4$ are each independently in each occurrence H, Cl, Br, I, $C_4H_4S$ (thiophenyl), $SO_3^-$, $CO_2^-$, C≡CH, CH≡$CH_2$, $NH_3^+$, OH, C≡N, $C_1$-$C_4$ alkyl, $(CH_2)_x$CH≡$CH_2$, or $(CH_2)_y$CH≡$CH(CH_2)_z$ where x or (y+z) is an integer of 0 to 4 inclusive, $(CH_2)_j$CH≡CH, or $(CH_2)_k$CH≡$C(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, thiol, amine (primary, secondary, tertiary or ammonium), hydroxyl, carboxyl, carbonyl, sulfonyl, or $C_2$-$C_4$ alkenyl; it is appreciated that the aforementioned alkyls, alkenyls, or alkynyls are each linear, branched or cyclic; $R^5$ and $R^6$ are each independently in each occurrence O or NH; and any partial bonds are completed by joining to complementary portions of other rings C or D to form a composite pore structure. This is illustrated with respect to specific OFNMs as detailed below. It is further appreciated that two or more R groups projecting into a nanopore are further reacted to create a bridging moiety therebetween to further modify nanopore size and functionality or chelate a metal ion. Bridging moieties include polyphenyls, and macromolecules such as a heteroaromatic, an amino acid, a fullerene, a glycol, a sugar, a dipeptide, a tripeptide, an oligopeptide, a protein, a nucleic acid, and a virus. These are exemplified below with respect to nanopore C of FIG. 12 and both nanopores of FIG. 13A.

A second inventive basic building block unit (II) is provided:

(II)

Figure 9:
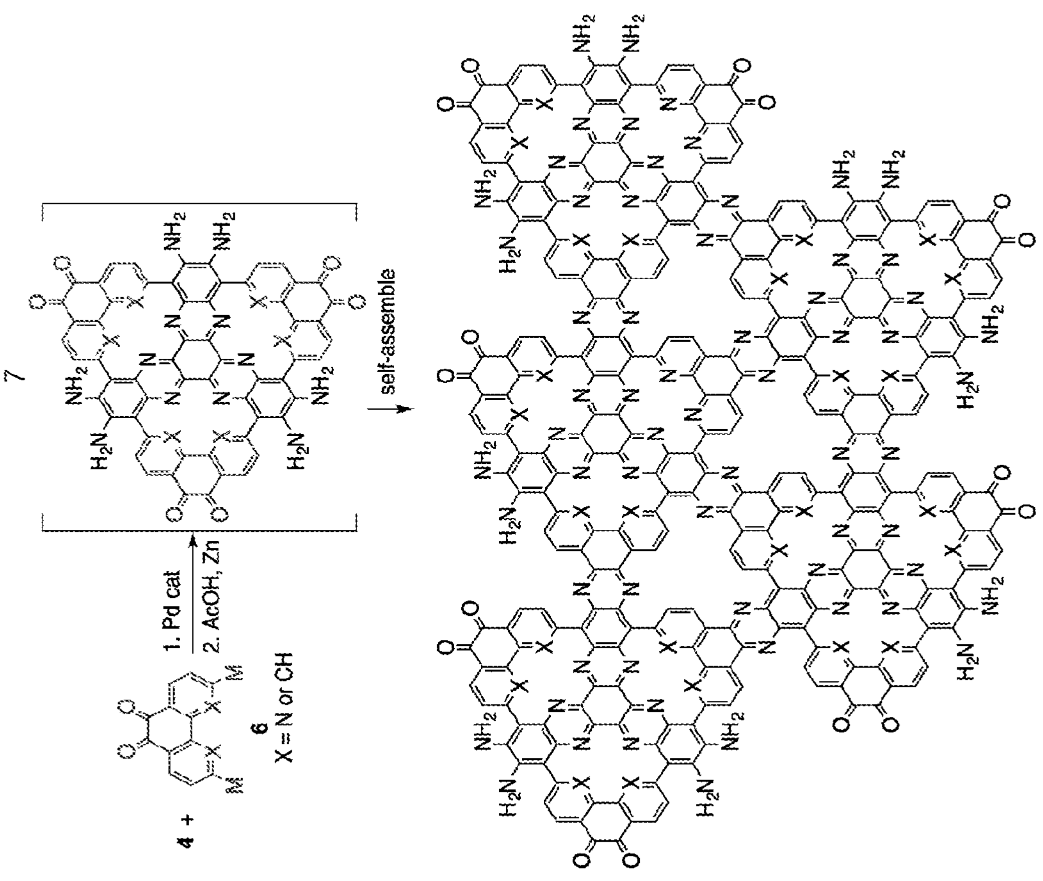
FIG. 9 illustrates the production of a two-nanopore material system in accordance with embodiments of the invention.

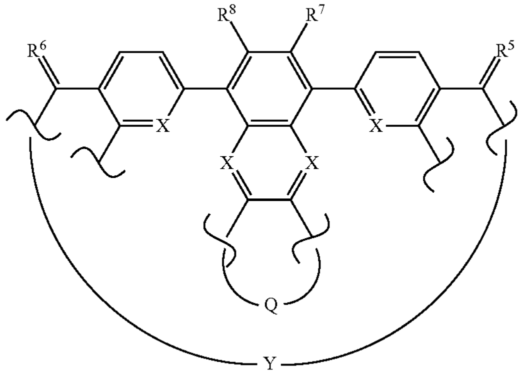

where R5 and R6 are each independently in each occurrence O or NH; $R^7$ and $R^8$ are each independently in each occurrence H, Cl, Br, I, $C_4H_4S$ (thiophenyl), $SO_3^-$, $CO_2^-$, C≡CH, CH≡$CH_2$, $NH_3^+$, OH, C≡N, $C_1$-$C_4$ alkyl, $(CH_2)_x$CH≡$CH_2$, or $(CH_2)_y$CH≡$CH(CH_2)_z$ where x or (y+z) is an integer of 0 to 4 inclusive, $(CH_2)_j$CH≡CH, or $(CH_2)_k$CH≡$C(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, thiol, amine (primary, secondary, tertiary or ammonium), hydroxyl, carboxyl, carbonyl, sulfonyl, or $C_2$-$C_4$ alkenyl; it is appreciated that the aforementioned alkyls, alkenyls, or alkynyls are each linear, branched or cyclic; X is independently in each occurrence an $sp^2$-hybridized carbon atom-H, methylene, N—H or a nitrogen atom with the proviso that at least one X is the N—H or the nitrogen atom, Q is an integer value of 3 to form a 6-membered ring, Y is an integer value of 3 to form trifold symmetry pores of bounded by 13 total carbon or nitrogen atoms. It is appreciated that through reaction of groups $R^7$ and $R^8$, a trifold BBU (II) is joined to other such units to form a CBU as shown in FIG. 9 with additional 26-member pores, or covalently bonded to immobilize or further functionalize the BBU (II).

A third inventive basic building block unit (III) is provided:

(III)

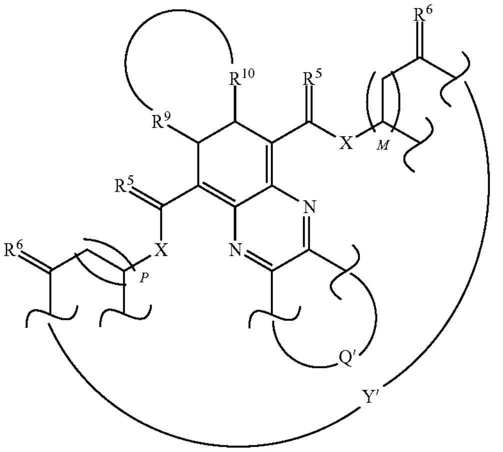

where $R^5$ and $R^6$ are each independently in each occurrence O or NH; $R^9$ and $R^{10}$ are independently in each occurrence H, Cl, Br, I, $C_4H_4S$ (thiophenyl), $SO_3^-$; $CO_2^-$, C≡CH, CH≡$CH_2$, $NH_3^+$, OH, C≡N, $C_1$-$C_4$ alkyl, $(CH_2)_x$CH≡$CH_2$, or $(CH_2)_y$CH≡CH$(CH_2)_z$ where x or (y+z) is an integer of 0 to 4 inclusive, $(CH_2)_j$CH≡CH, or $(CH_2)_k$CH≡C$(CH_2)_r$ where j or (k+r) is an integer of 0 to 4 inclusive, and where $R^9$ and $R^{10}$ bonded together are —N═C($R^{11}$)C($R^{12}$)═N—, —N—SN—, —N—O—N—, and form a five-, or six-membered ring; $R^{11}$ and $R^{12}$ are independently in each occurrence R and $R^2$, respectively or combine to form polycyclic of triphenyl-2, 3, 6, 7 tetraone; where the aforementioned alkyls, alkenyls, or alkynyls are each linear, branched or cyclic; and those variables common to above structures as are defined as detailed above; X is independently in each occurrence an $sp^2$-hybridized carbon atom —H, methylene, N—H or a nitrogen atom; P and M are each independently the structure as shown absent the parentheticals (equal to 1) or includes an additional —$(CH_2\acute{C}HCHCH_2)_{1-3}$— or —$(CH\acute{C}\acute{C}CH)_{1-3}$ that forms an additional 1 or 2 or 3 6-membered aliphatic or aromatic rings in each occurrence resulting in tetracyclic to a enneacyclic central structure in structure (III), $\acute{C}$ denotes an $sp^3$- or $sp^2$-hybridzed carbon with a bond fragment extending to complete a pore through repetition of unit structure (III) as needed via Y'; Q' is an integer value of 3 to form a 6-membered ring; Y' is an integer value of 3 forming a pores inclusive of the clefts between P and Q', and between M and Q'. This is illustrated in exemplary form with respect to FIG. 10. It is appreciated that $R^9$ and $R^{10}$ are reacted to couple BBUs together to form extended crystalline structures in two or three dimensions.

A fourth inventive basic building block unit (IV) is provided:

(IV)

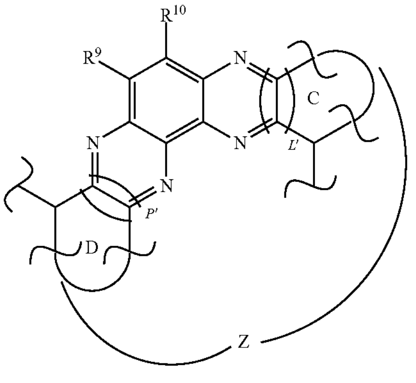

where $R^9$ and $R^{10}$ are each independently in each occurrence H, Cl, Br, I, $C_4H_4S$ (thiophenyl), $SO_3^-$, $CO_2^-$, C≡CH, CH≡$CH_2$, $NH_3^+$, OH, C≡N, $C_1$-$C_4$ alkyl, $(CH_2)_x$CH≡$CH_2$, or $(CH_2)_y$CH≡CH$(CH_2)_z$ where x or (y+z) is an integer of 0 to 4 inclusive, $(CH_2)_j$CH≡CH, or $(CH_2)_k$CH≡C$(CH_2)$, where j or (k+r) is an integer of 0 to 4 inclusive, and where $R^9$ and $R^{10}$ together are —N═C($R^{11}$)C($R^{12}$)═N—, —N—S—N', —N—O—N—, and form a five-, or six-membered ring; $R^{11}$ and $R^{12}$ are independently in each occurrence R and $R^2$, respectively or combine to form polycyclic of triphenyl-2, 3, 6, 7, tetraone, where the aforementioned alkyls, alkenyls, or alkynyls are each linear, branched or cyclic; P' and L' are each independently the structure as shown absent the parentheticals (equal to 1) or includes an additional —$(CH_2\acute{C}HCHCH_2)_{1-3}$— or —$(CH\acute{C}\acute{C}CH)_{1-3}$ that forms an additional 1 or 2 or 3 6-membered aliphatic or aromatic rings in each occurrence resulting in tetracyclic to a enneacyclic central structure in structure (III), $\acute{C}$ denotes an $sp^3$- or $sp^2$-hybridzed carbon with a bond fragment extending to complete a pore through repetition of unit structure (IV) as needed via Z; Z is an integer value of from 3 to 6; and those variables common to above structures as are defined as detailed above.

In some inventive embodiments of BBUs (I), (II), (III), or (IV), X is uniformly a nitrogen atom in every occurrence. In still other embodiments of BBUs (I), (II), (III), or (IV), X is uniformly NH in every occurrence. In still other inventive embodiments, the BBUs (I), (II), (III) or (IV) self-assemble into an inventive OFNM. In still other inventive embodiments, the BBUs (I), (II), (III) or (IV) are polyaromatic. In still other inventive embodiments, the BBUs (I), (II), (III) or (IV) are perfluorinated. In still other inventive embodiments, the BB Us (I), (II), (III) or (IV) chelate an atom or an ion, such as a main group metal ion, transition group metal ion, lanthanide series metal ion, or combinations thereof.

The control of nanopore number, size, and chemistry through modification of R groups allows for the formation of a crystalline materials of a near endless number of configurations, inventive OFNMs are ideal for battery electrodes since they, due to their rigidity and stability and electronic conductivity, have almost no dimensional changes upon charge/discharge cycles and can be designed with nanopores to be selective for transporting and storing a particular high energy redox species such as ions of Li, Na, Al or Ca. Since inventive OFNMs can be prepared with nanopores through control of R groups to selectively bind and transport anions, inventive OFNMs are also useful as membranes for conventional transition metal containing redox flow batteries. It is appreciated that by stacking layers of anion and cation specific materials including inventive OFNMs results in a bipolar membrane. The ability to also incorporate electrocatalysts into specifically designed binding sites within the same inventive OFNM material could revolutionize fuel cell and electrolyzer designs by incorporating electronic conduction, ion transport, electrocatalysis and gas transport within the same material.

The inventive OFNM materials are well-suited for operation in a battery. The ability to construct specific sized and functionalized channels for redox couples such as lithium and sodium in a highly conducting scaffold is extremely beneficial. The problem of charging cycle life is often due to morphological changes in the battery electrodes whether they are anodes or cathodes. The rigid 2D structure of the inventive OFNM materials and their high stability circumvent this problem. Although the pure materials are predicted to be semiconducting, reduction of cations used in batteries such as lithium transform the materials into a conductor by putting electrons into the conduction band and inserting the metal into the channels. The theoretical studies are able to predict the semiconductor metal transition and what ions can be accommodated in the various structures and help guide the synthesis targets. The new OFNM materials may be synthesized in gram scale quantities for evaluation in button cells, often used by groups that evaluate new materials for battery electrodes.

The inventive OFNMS with a combination of tunable chemical sensitivity of the nanopores and semiconducting properties also makes these materials attractive in chemical sensing. The high quality PETs constructed with thin layers of g-$C_2N$ suggests that the gated current flow in a device, constructed with embodiments of the inventive materials, combined with the chemical selectivity that can be incorporated in the nanopores, make these materials useful for PET based sensors. Such measurements can be combined with the ion selective membrane measurements but done on single or multiple layers of the synthesized 2D materials on a Si/$SiO_2$ substrate with e-beam lithography deposited source and drain electrodes as done in the previous study on g-$C_2N$. Most PET sensors operate with only a monolayer of chemical functionality to influence the current flow whereas the chemical functionality of embodiments of the inventive materials are incorporated throughout the bulk of the materials and so single layers would not be required.

Heterogeneous catalysis and electrocatalysis are another promising application of embodiments of the inventive materials. The catalysis could operate as designed heterogeneous catalyst supports since the binding of catalytically active metal atoms in the functionalized nanopores will produce identical catalytic sites, unlike most supported catalysts where there is polydispersity in the metal clusters. Of particular interest in catalytic studies are the "two nanopore" systems where two nanopores can be designed to bind several different metals that each perform a separate role in a catalytic reaction such as substrate binding, electron transfer, or proton transfer. The conducting nature of these nitrogenated structures allow them to be used directly as electrocatalytic electrodes in fuel cell or electrolysis cells that require multistep electron-proton coupled reactions that usually use a carbon support for small metal clusters of active metals such as Pt.

Embodiments of the inventive structure may be used as a graphene-based filter with an ordered structure to filter chemicals, viruses, or bacteria from a range of liquids including water that requires filtration for consumption. Embodiments of the forming techniques described herein allow for filters to be produced much faster and in larger sizes, which is critical for developing commercial applications.

Several types of inventive OFNMs are synthesized through the formation of imines. Imine formation is dependent on multiple factors such as solvent, time, temperature, pH, order, and stoichiometry of added reagents that control yield, crystallinity, and size of the crystalline domains. For example, imine formation is typically fastest at a pH of 4-6, where a lower pH results in amine protonation, and a higher pH results in inhibited protonation of the OH leaving group, both of which slow down the reaction. The use of PH levels is used in the present invention to induce and control the growth of the material. Furthermore, because this is a reversible reaction, formation of the more thermodynamic product can be controlled.

Figure 5:
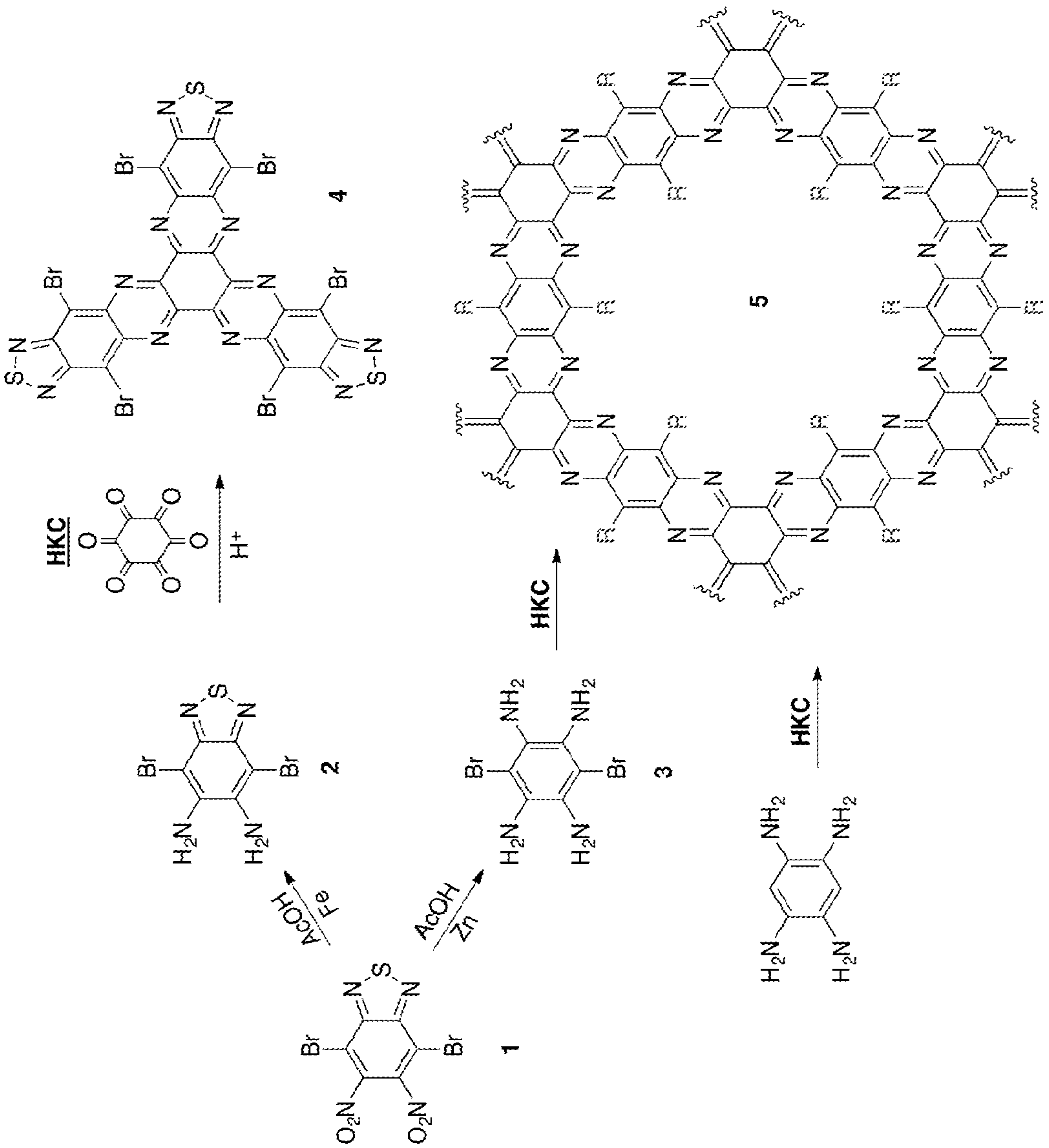
FIG. 5 illustrates a new analog of the g-$C_2N$ material of FIG. 4 formed via three key reactions in accordance with embodiments of the invention.

FIG. 5 illustrates an embodiment of the new OFNM formed by the reaction of 4,7-dibromo-5,6-dinitro-2,1,3-benzothiadiazole (1) and either tetraaminobenzene or dibromotetraaminobenzene (3) in hexaketocyclohexane (HKC) to give OFNM (5) based on basic building unit (I). Embodiments of the inventive process utilize synthetic modifications of bromine containing OFNM (5) that are accomplished via metal-catalyzed transformations of the bromine containing ordered nanoporous OFNM enabling bromine substitution and functionalization of the material. The nature of the catalyst is shown in FIG. 5 to affect the nature of the synthetic product with iron catalyzed reaction of HKH in acetic acid (AcOH) yielding 4,7-dibromo-5,6-diamino-2,1,3-benzothiadiazole that reacts with HKC under acidic conditions to yield the three-fold plane of symmetry monomer (4). In certain inventive embodiments, a scheme is applied to synthesize a new form of two dimensional (2D) OFNM with two chemically distinct nanopores, where the nanopores are each independently capable of subsequent chemical modifications to enable the implementation of desired functions.

Figure 4:
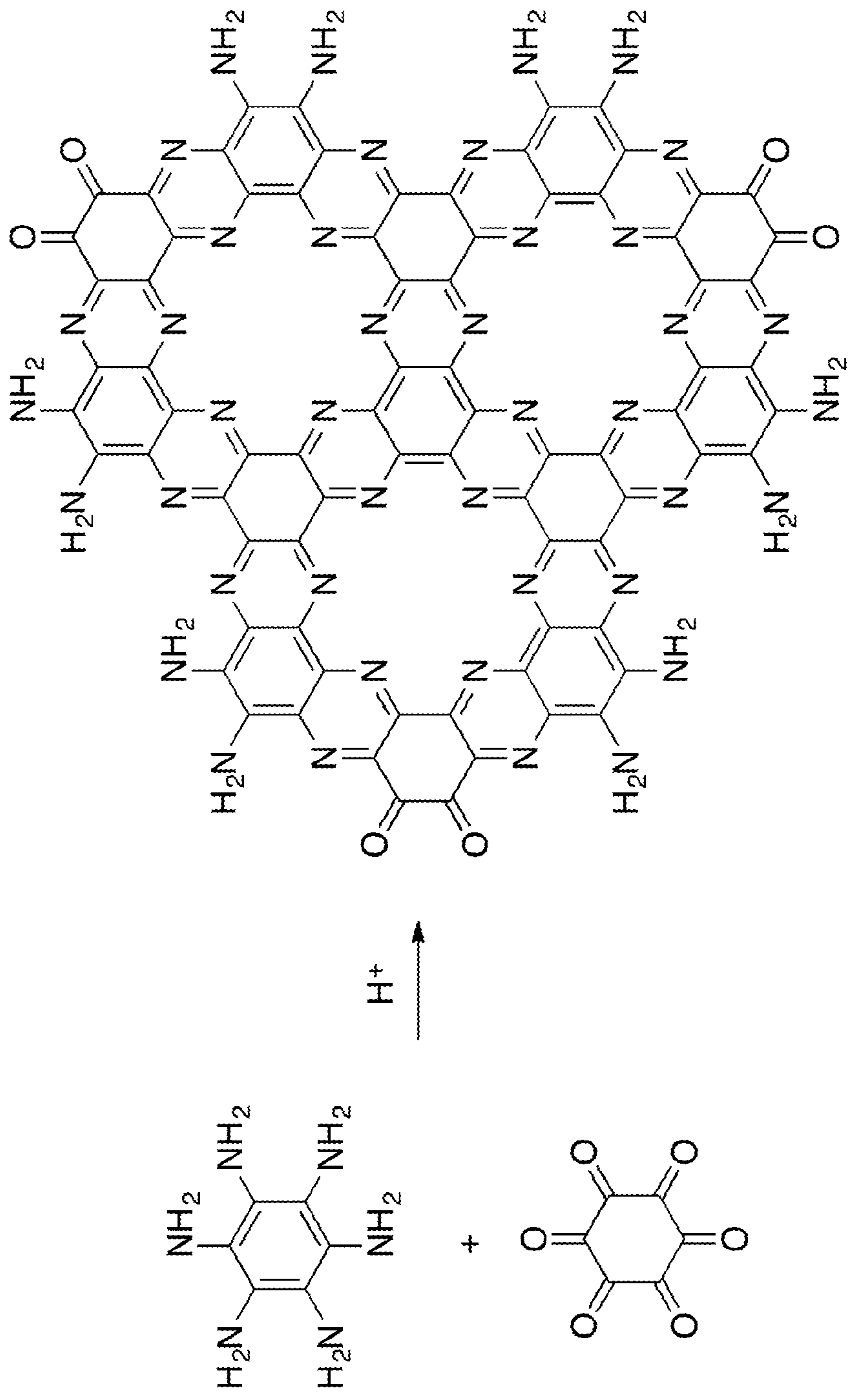
FIG. 4 illustrates a prior art reaction to form a g-$C_2N$ material that it is made using a condensation reaction between a ketone and amine at lower temperatures to form imine moieties.

FIG. 5 illustrates a new analog of the g-$C_2N$ material of FIG. 4 formed via three key reactions. Dibromo (1), the principal building block specific to synthetic modifications of a new OFNM via metal-catalyzed transformations is prepared according to a three-step procedure. Using inexpensive o-phenylenediamine, (1) is obtained in an overall 75% yield using classic aromatic substitution chemistry. Two convenient manipulations are known for 1 and involve selective reduction of the nitro groups to produce diamine (2) or global reduction to give tetraamine (3). Reaction of (2) with HKC in a 3:1 ratio results in (4) in 77% yield. In confirming the structure of (4), mass spec analysis was most definitive in that the six bromine atoms gave the expected and distinctive isotope pattern along with the correct molecular weight. Additionally, this two-step reaction may be preformed in a one-pot reaction. Thus, (1) was mixed with HKC, acetic acid in the presence of iron to give (4).

Figure 7:
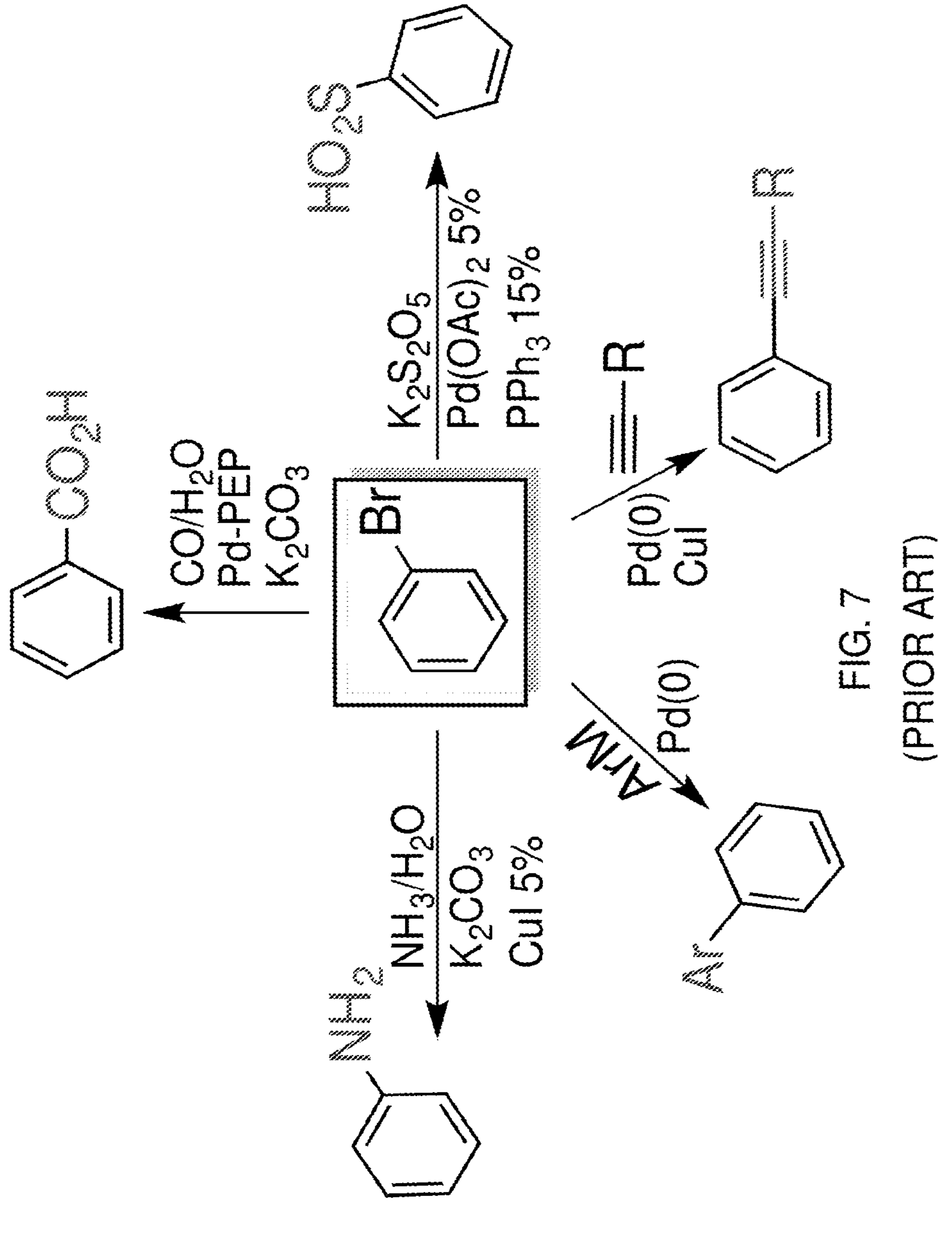
FIG. 7 illustrates prior art transformation using metal catalyzed substitutions of aryl bromines in accordance with embodiments of the invention.

Continuing with FIG. 5, two new analogs of a 2D OFNM in the form of $C_2N$ OFNM have also been synthesized under modified conditions using a reaction of HKC with 1,2,4,5-tetraaminobenzene to yield (5), where R=H, while reaction of (3) with HKC produced (5) with R═Br (depicted as a single nanopore). The brominated pore is particularly useful as an easily substituted group to produce different pore functionalities and have already been synthesized as a carboxylated pore (shown as D in FIG. 12) and via other reaction schemes as detailed below and summarized in prior art FIG. 7.

Figure 6A:
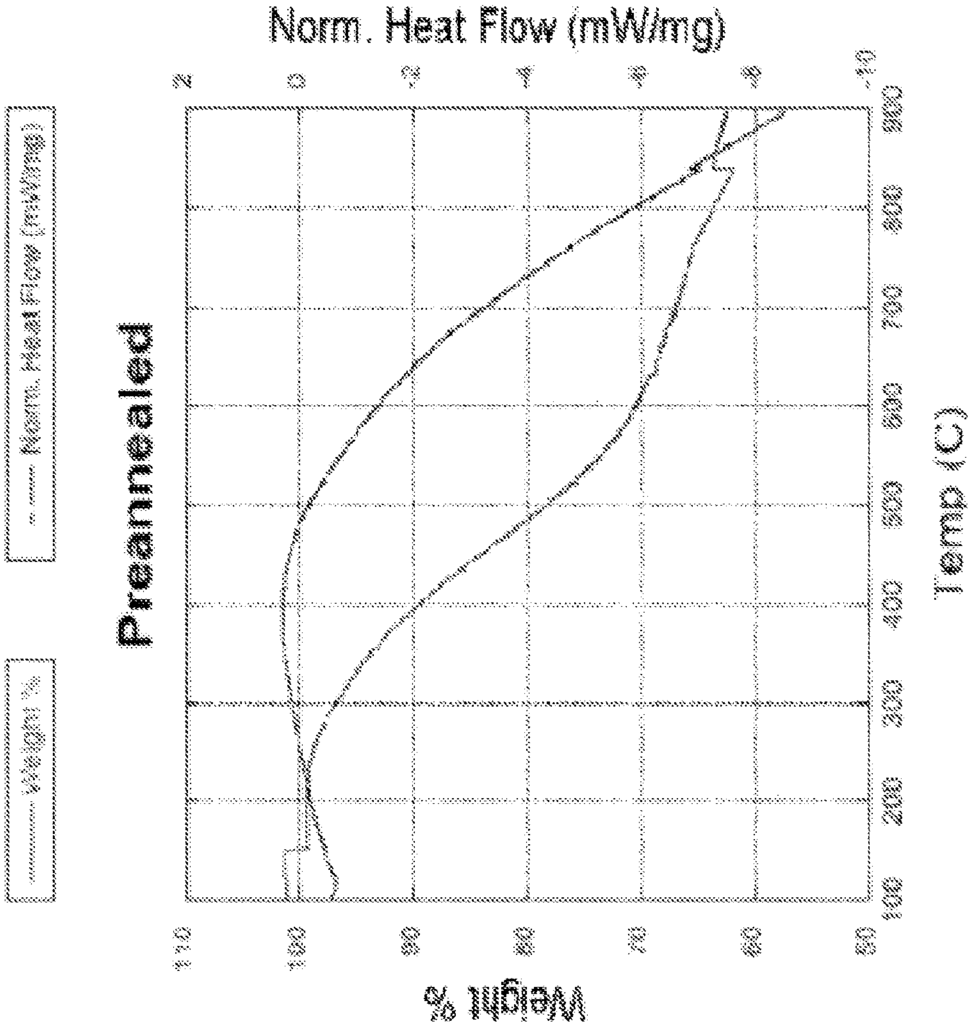
FIG. 6*a* is a graphical representation of a thermogravimetric (TGA) analysis and differential scanning calorimetry on pre-annealed material (5), R=H of FIG. 5.
Figure 6B:
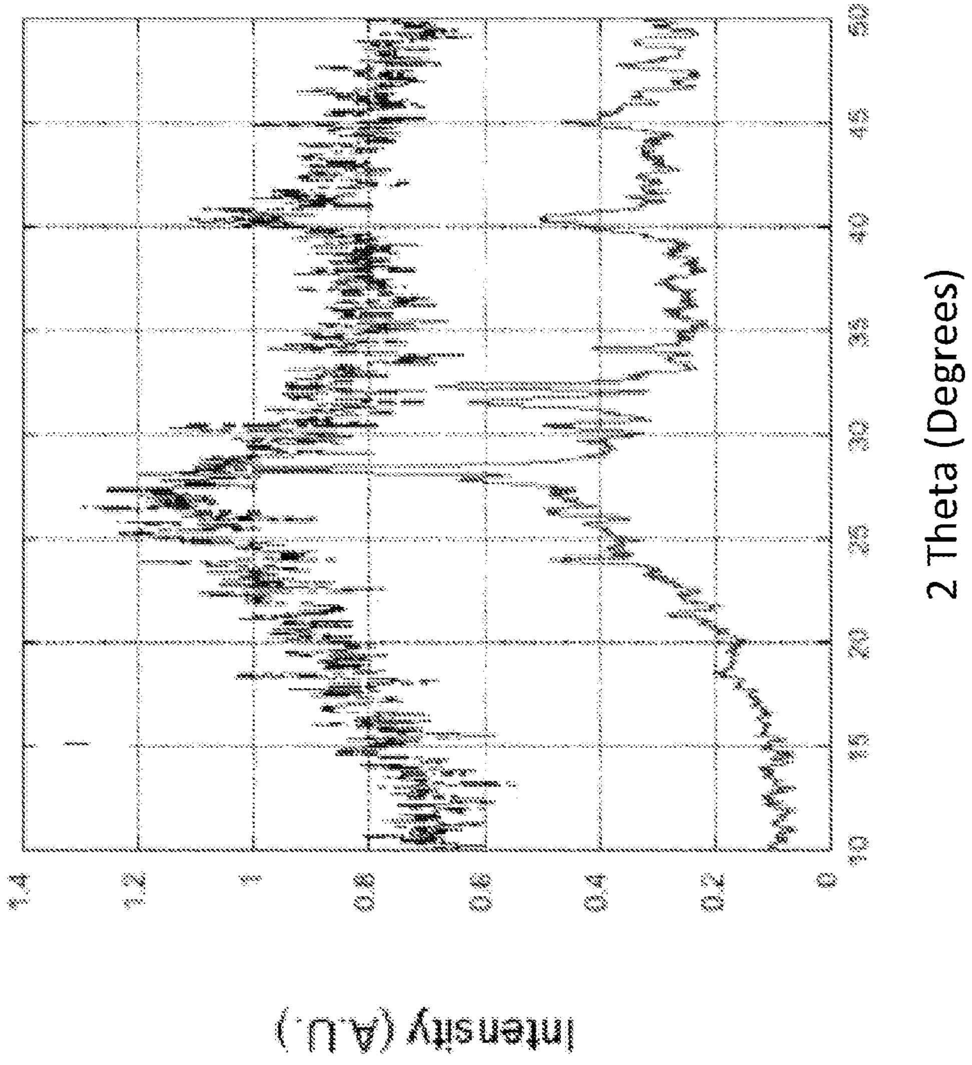
FIG. 6*b* is a graphical representation of powder x-ray data of pre-annealed and annealed material (5), R=H of FIG. 5 in accordance with an embodiment of the invention.
Figure 6C:
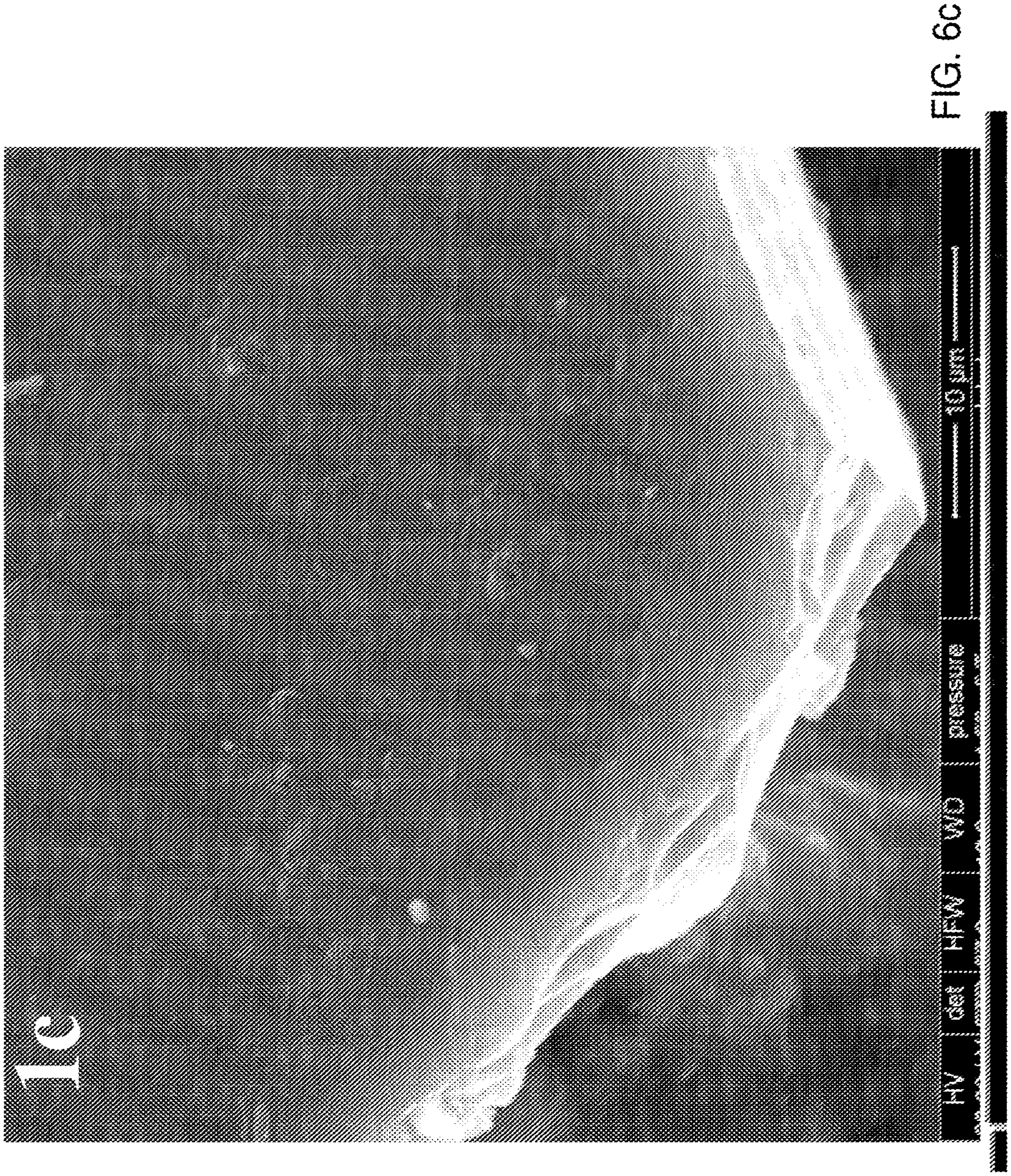
FIG. 6*c* is a scanning electron microscope (SEM) image of annealed (5), R═H of FIG. 5 in accordance with an embodiment of the invention.
Figure 6D:
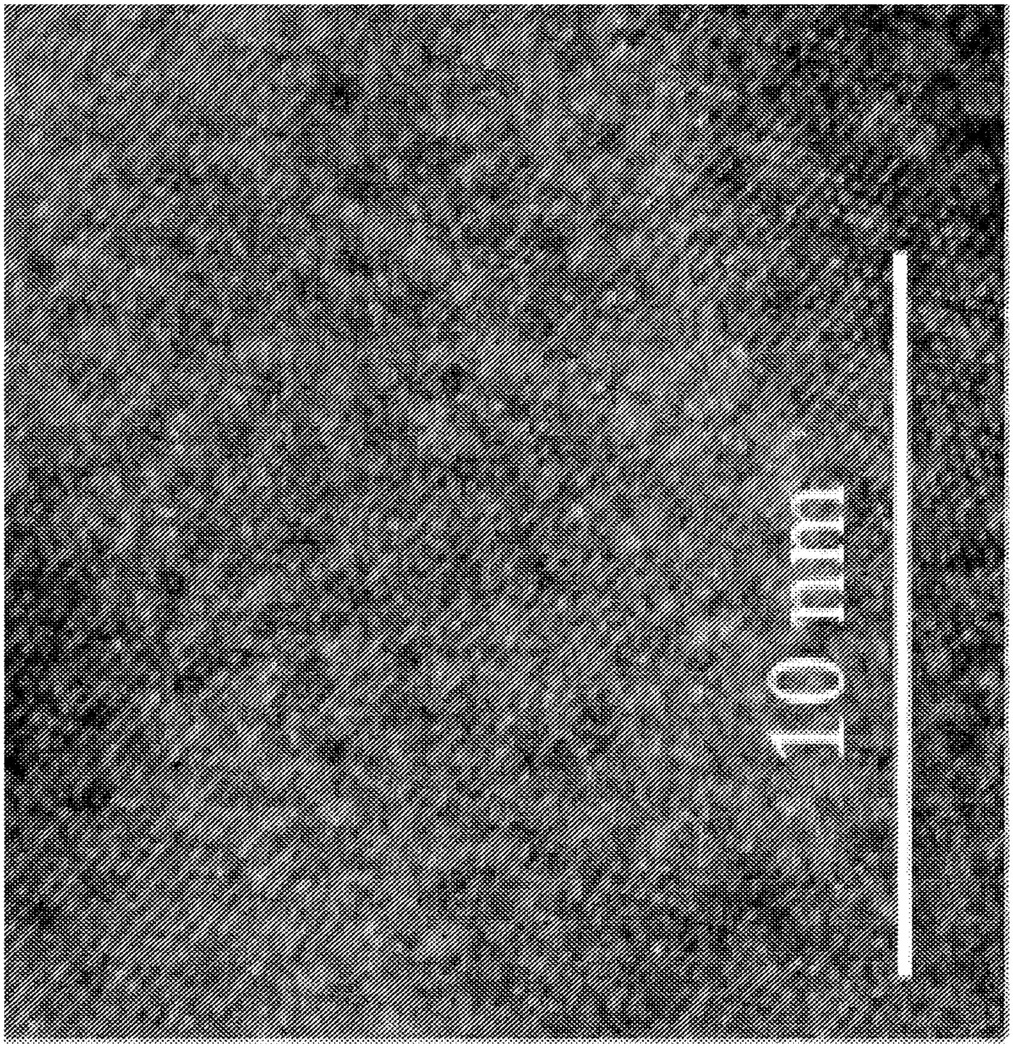
FIG. 6*d* is a transmission electron microscopy (TEM) image of thin flakes of (5), R═H of FIG. 5 revealing a hexagonal lattice structure in accordance with an embodiment of the invention.
Figure 6E:
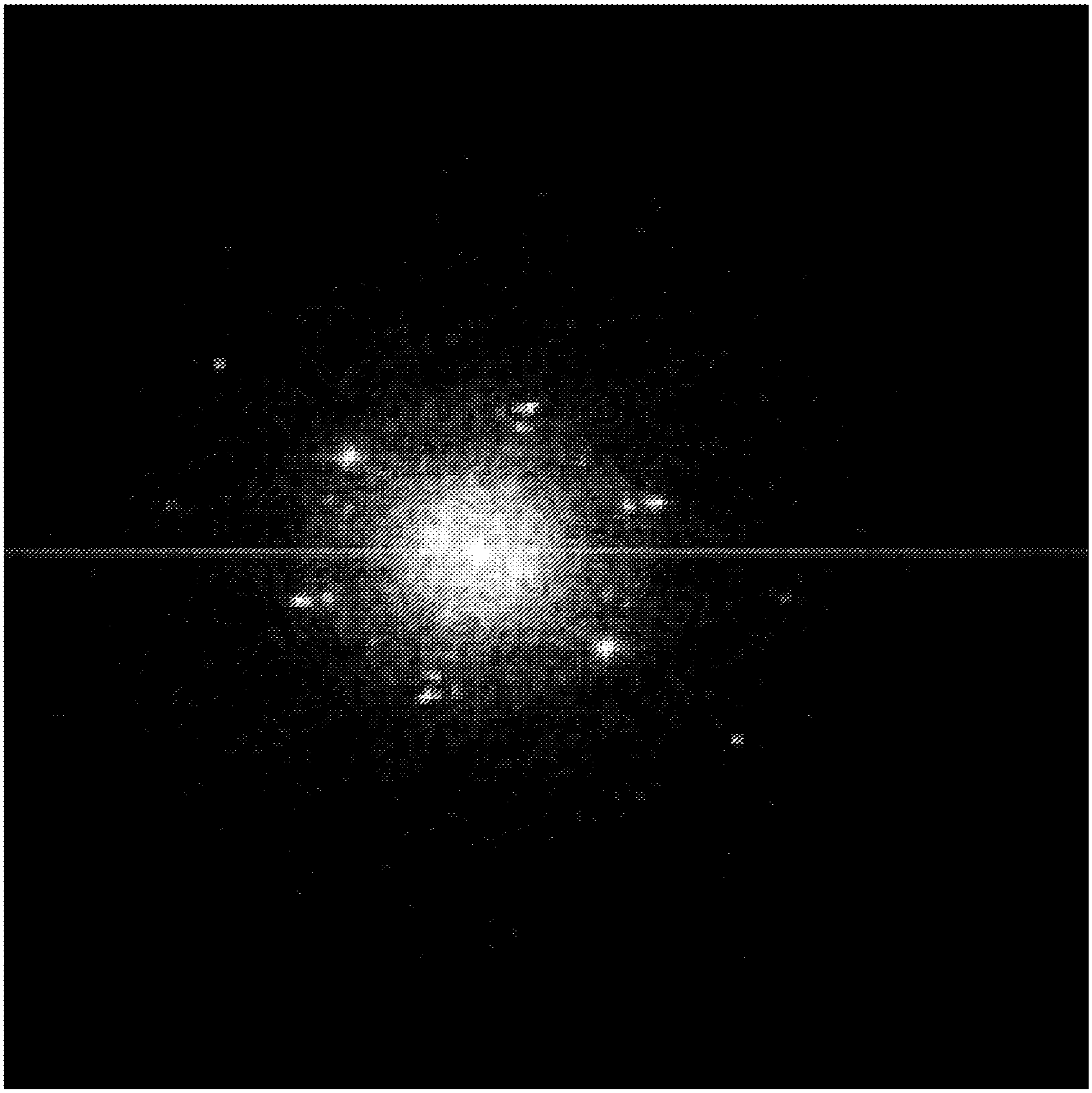
FIG. 6*e* is a 2D fast Fourier transform (FFT) of the TEM image of FIG. 6*d* showing hexagonal symmetry with some multiplicities in the spots in accordance with an embodiment of the invention.
Figure 6F:
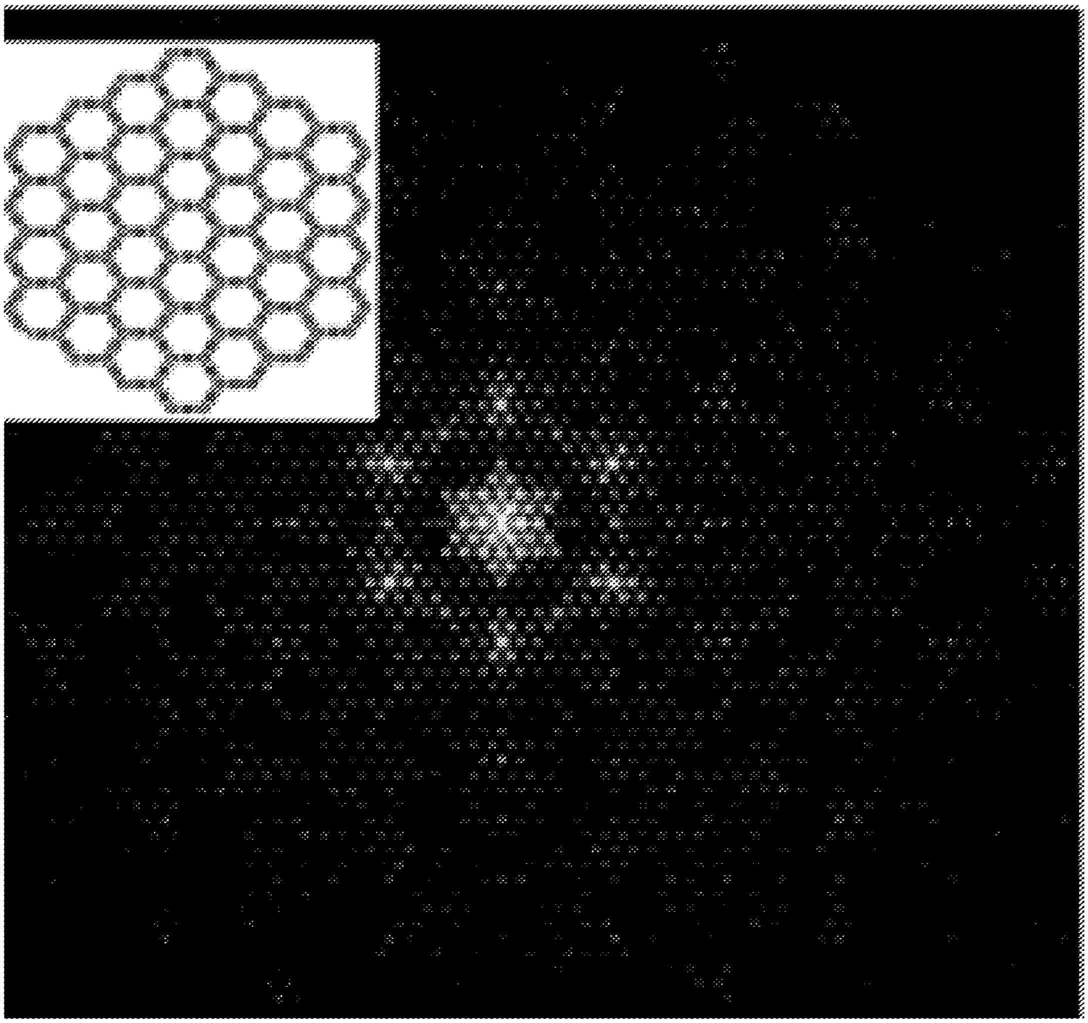
FIG. 6*f* is a simulated 2D-FFT of a nanoporous hexagonal network of rings for (5), R═H in accordance with an embodiment of the invention.

The structure of (5), R═H was established via solid-state NMR, TEM and X-ray diffraction. While the rate of addition of the amine has been modified, there is considerable optimization of this reaction yet to be accomplished. Solid state NMR displayed a large aromatic CH resonance at 130 ppm, and quaternary at 170 ppm. No resonances downfield of 200 ppm were observed, and any additional resonances between 180 and 200 were hidden by the spinning side bands. A specific protocol involves boiling the reagents with acid catalyst, filtration and then subjecting the black material to an annealing process by heating to temperatures up to 730° C. in inert gas. Thermogravimetric (TGA) analysis of pre-annealed material revealed a loss of 35% of mass per FIG. 6*a*, whereas the annealed sample showed only a 5% loss at the identical temperature and only a 10% loss at 900° C. As shown in FIG. 6*b*, X-ray data revealed broad peaks on the pre-annealed (above scan) material that sharpened upon annealing (lower scan) to give a spacing (3.37 Å) nearly identical to that reported for g-$C_2N$ (3.28 Å) or graphite (3.35 Å) indicating a stacking of layers in the bulk solid. Some unidentified peaks are observed in the annealed XRD pattern. SEM images of (5), R═H per FIG. 6*c* showed regions that appeared to have a laminar structure with some facets with 120° angles indicating a hexagonal structure. Solid-state NMR confirmed these changes to the material after annealing, in which two different aromatic proton resonances were observed. The major peak is assigned to the inside shielded protons and a small shoulder to the peripheral aromatic de-shielded protons. The ratio of these two resonances may be an indication of the average crystallite size. Extensive sonication (>4 hrs) in dimethylformamide (DMF) or dimethyl sulfoxide (DMSO) of the annealed material was sufficient to exfoliate and suspend the material so thin flakes could be transferred to a TEM grid and other exfoliation chemistry may be able to primarily produce single sheets as is possible with other 2D materials. TEM images of thin samples revealed a hexagonal lattice structure per FIG. 6*d*. FIG. 6*e* illustrates a 2D fast Fourier transform (FFT) of image FIG. 6*d* showing hexagonal symmetry with some multiplicities in the spots. FIG. 6*f* is a simulated FFT based on the hexagonal network of chains of (5) (inset) as an approximation of the structure of a porous OFNM.

Finally, pre-annealed material dissolves/suspends in solvents such as DMF, DMSO but the annealing process produces a glittery mica-like material in suspension and a black material with shiny faces in the bulk. Thus, it may be preferable to perform synthetic modifications at the pre-annealed stage. In order to illustrate that the proposed transformations are feasible, a carbonylation of (5), R—Br was performed to produce the carboxylic acid derivative (5), R═$CO_2H$. Thus, (5), R═Br was treated with $PdCl_2(PPh_3)_2$, $K_2CO_3$, 1 atm CO, $H_2O$/DMF at 90° C. for 3 days then precipitated, filtered and dried. Infrared (IR) scan of the black solid displayed a new C═O stretch at 1655 $cm^{-1}$, and a broad OH stretch from 3200-2800 $cm^{-1}$, both of which are consistent with a H-bonded carboxylic acid.

While chemically transforming polymers is usually not straight forward, however with the incorporation of bromines in (5), in embodiments of the invention, provides that ability. Metal catalyzed substitutions of aryl bromines are a well-established transformation with typical examples illustrated in FIG. 7. These reactions are all well-established in both the academic and industrial realms. Carbonylation, sulfonation, and amination can all be accomplished via the use of standard metal catalysis (e.g., Pd, Ni, Cu) or using catalysts bound to resins (PEP), all under mild conditions such as room temperature, atmospheric pressure, and in a range of solvents. Coupling of aromatic rings (Ar), both heteroaromatic and substituted benzene derivatives, are common procedures via reactions developed by Stille, Suzuki-Miyaura, or Negishi. Miyaura, N. et al., Chemical reviews, 95 (7): 2457-2483 (1995). Coupling of alkynes is also a very facile reaction via Sonogashira conditions. Furthermore, these reactions are compatible with solid-phase chemistry and thus may be amendable to the materials formed in embodiments of the invention.

Figure 8:
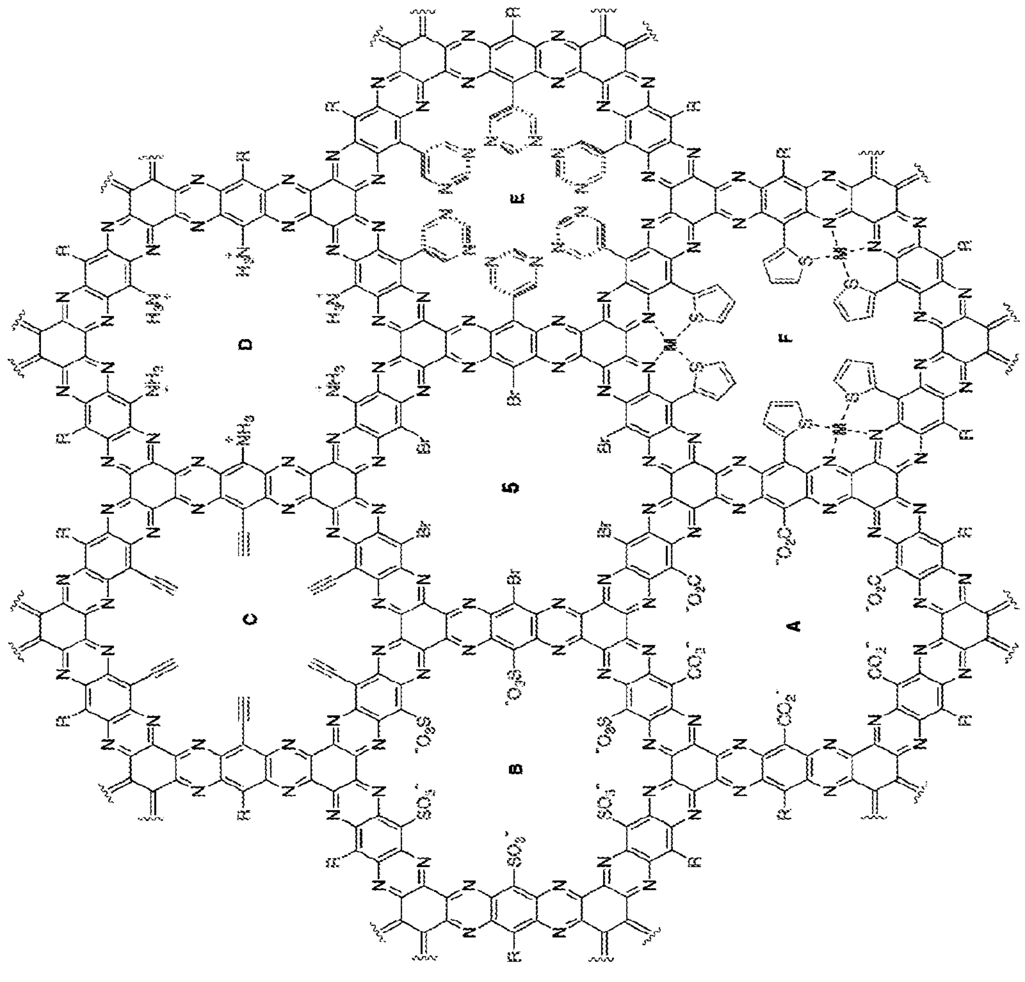
FIG. 8 illustrates the diversity of transformations using the above metal-catalyzed reactions for OFNM (5), R═Br, and is a composite drawing of various nanopore functionalization in accordance with embodiments of the invention.

FIG. 8 illustrates the diversity of transformations using the above metal-catalyzed reactions for OFNM (5) (R═Br). The middle nanopore depicts the original starting material with the bromines, while the six peripheral nanopores (A-F) illustrate the subsequent transformations. It is appreciated that the depicted mixed polymer shown in each indicated transformation is exemplary of what specific reaction may be performed on the entire structure, and is a composite drawing of various nanopore functionalizations. Alternatively, through resort to protecting group chemistry, a mixed nanopore functionalization is achieved. The use of protecting groups to selectively modify only a portion of the total functionality is well-known in the field, as for example, detailed in Greene's Protective Groups in Organic Synthesis, Fourth Edition, by Peter G. M. Wuts, Theodora W. Greene, Print ISBN: 9780471697541, DOI: 10.1002/0470053488 (2006).

With respect to FIG. 8, nanopores A and B both provide for negatively charged nanopores of a multipore version of (5). Nanopore D provides a positively charged nanopore that can be generated via a palladium-catalyzed amination followed by protonation of the resulting primary amine. Additionally, inclusion of alkynes of nanopore C provides a template to perform click chemistry, such as Huisgen dipolar cycloadditions. The effect of this would be to add steric bulk and thus prevent close stacking. Furthermore, once heteroaromatic structures such as nanopore E and F are formed, complexation to metals, in nanopore F, will be carried out. Interestingly with nanopores E and F, the cyclics (pyrimidine and thiophene) must twist to orientate perpendicular to the sheet. This has the potential to coordinate a metal between sheets via coordination of pyrimidine nitrogen or the sulfur atoms. Additionally, depending on the substituted group stacking of the materials into 3D layered structures will be inhibited and/or the layer spacing will be increased. Preventing stacking will make measurements of single layer properties, and constructing devices based on single layers, much easier. Substituted nanopores with groups that might interact with other layers via hydrogen bonding (for example, carboxylic acids) would favor stacking polytypes with no nanopore offsets between the layers making ion transport more facile. Use of nanopore D, where the amine groups are neutral, can also serve as a metal complexation material. It is appreciated that not all nanopores will be formed with 100% substitution of the bromide, but rather are optimized based on the reaction conditions. Variation of conditions to control substitution illustratively include: reaction time, pH, intermediate reaction with protecting group addition/removal, rate of addition of reagents, solvent choice and annealing time.

Figure 12:
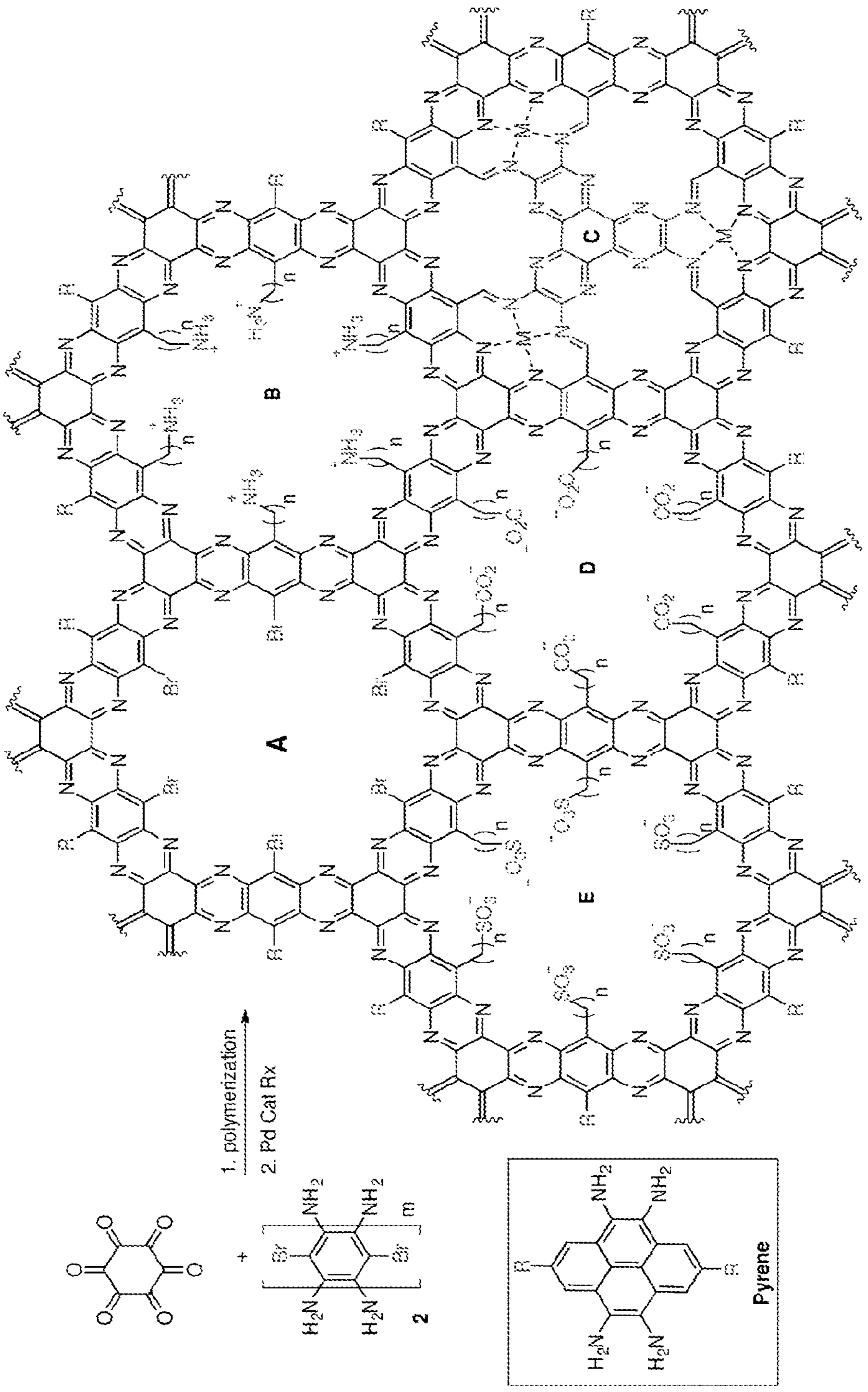
FIG. 12 further illustrates the diversity of transformations using the above metal-catalyzed reactions for OFNM (5), R═Br as was shown in FIG. 8, and is a composite drawing of various nanopore functionalization in accordance with embodiments of the invention.

FIG. 12 illustrates an additional inventive embodiment of a diversity of transformations using metal-catalyzed reactions for an OFNM. Nanopore A depicts the original starting material (R═Br), while nanopores B-E illustrate exemplary transformations. It is appreciated that like FIG. 8, FIG. 12 is a composite of indicated transformations; however, as noted above, with resort to protecting group chemistry. Mixed functionality within a given inventive OFNM is readily achieved. The size and aromatic delocalization of the framework may be varied by using tetraamine substituted polyaromatics by increasing m in precursor (2) or with other aromatic scaffolds such as pyrene (lower left in FIG. 12). The interior of the nanopore may be tuned by changing n from Oto longer more hydrophobic chains and to multiple pore sizes for smaller ions or metal (M) binding as in nanopore C.

It is evident that the new class of OFNM based materials may be developed to significantly impact many future energy technologies, including chemically selective ion conductive membranes, sensors, battery electrodes and catalysts. Membrane fabrication and characterization with the transformations depicted in nanopores B, D and E, shown in FIG. 12. Relative to challenges often encountered with OFNMs, including their microscopically corrugated molecular texture and non-ordered structures with considerable defects/holes in the sheet plane, the proposed OFNMs offer ordered supramolecular structures that can be aligned into membranes with tunable pore size on a truly molecular level, as shown in nanopore C. Membrane casting techniques have been used to fabricate graphene related membranes, due to their structural similarity to OFNMs. In a specific embodiment, macroscopic membranes are prepared by orientating supra-molecules/microcrystals as nematic phases by techniques illustratively including shear alignment, or voltage bias or vacuum filtration through a porous support. Proton conductivity is measured first with materials containing pores D and E to explore ion transport mechanisms in cast OFNM membranes as membrane electrolytes for polymer electrolyte membrane fuel cells (PEMFC) and electrolyzers to compare with current high-proton conductivity materials such as NAFION®. The ability of the inventive OFNM materials to operate at higher temperatures (100-150° C.) addresses the challenge of platinum (Pt) poisoning by carbon monoxide, and increases PEM fuel cell efficiency. More importantly, minimizing structural imperfections, including defects, alignment, and random pore size distribution, removes barriers to quantitatively correlating molecular pore architecture with macroscopic membrane performance. This ability to correlate molecular structure with macroscale function, together with knowledge gained from OFNM membrane casting and characterization, enables the rapid extension of these functional materials to many other applications, including lithium and alkaline ion conductors, low-cost and selective battery separators, and bipolar membranes.

Embodiments of the invention have established reaction conditions that optimize yield, molecular weight, and a degree of order in the materials to assure their stability, selectivity for ions and gases, and a high conductivity. With these conditions optimized, the already inexpensive starting materials become even cheaper if produced in large quantities leading to replacement of more costly and lower performance materials, such as Nafion®, in many electrochemical energy conversion technologies.

Formation of Two-Nanopore Materials

The formation of two-nanopore materials as shown in FIG. 9 may be accomplished using the monomer (4) that may be expanded to produce an inventive two-nanopore system. Metal-catalyzed coupling of (4) with 1,10-phenanthroline or phenanthrene diketo derivatives (6) followed by removal of the thiadiazole protecting group will provide intermediate (7) of FIG. 9. Monomer (7) includes diketo and diamine units and under the acidic conditions present is expected to self-assemble into a graphitic material (8). This material has two different nanopores throughout the ordered system with the two nanopores having distinct geometries, nanopores A and B are labeled in the scheme. This distinction enables the chemical modification of one nanopore in preference to the other. For example, coordination of a metal to the four nitrogen atoms when X=N should be facile. Metal versions (M=$B(OH)_2$ or Sn) of both the phenanthroline and phenanthrene derivatives (6) are readily available from commercial dibromo precursors and similar condensation/couplings of diketone derivatives of (4) in high yields have been performed. The system of FIG. 9 may also be easily modified to give a range of new OFNM materials as shown in FIG. 10.

Figure 10:
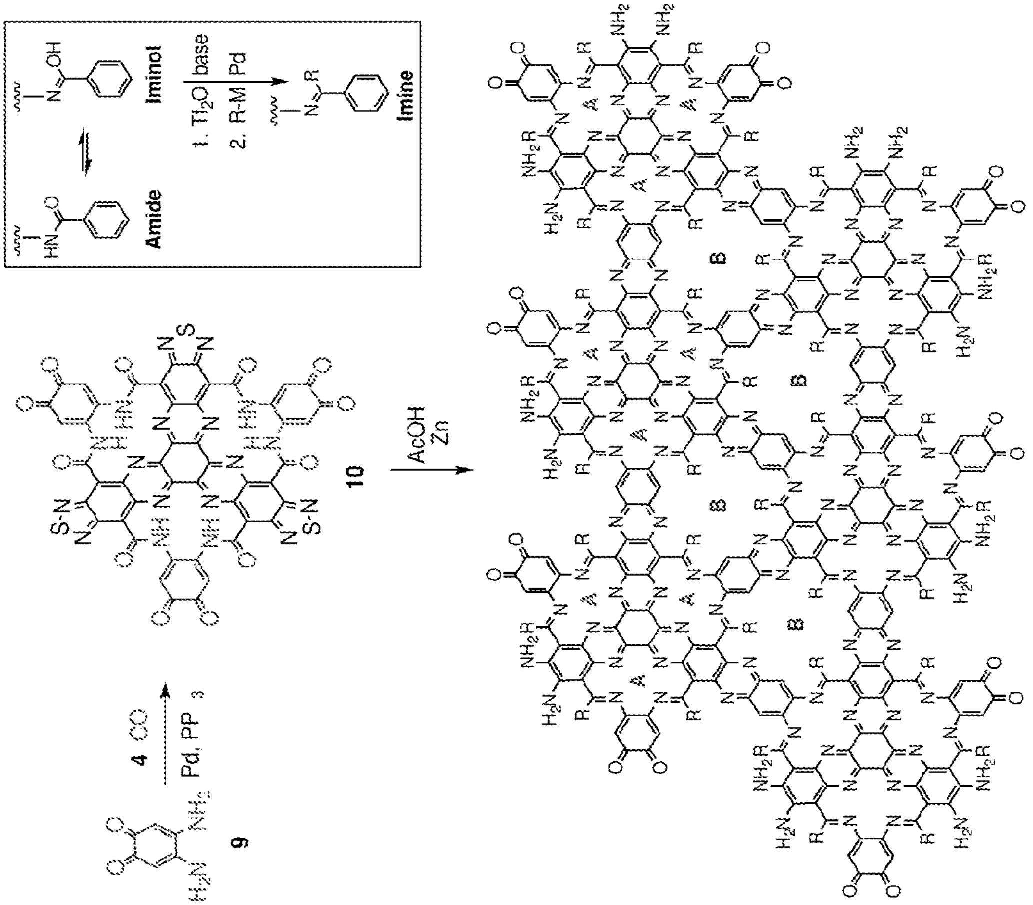
FIG. 10 illustrates the self-assembly of a monomer consisting of diketo and diamine units with subsequent metal-catalyzed functionalization in accordance with embodiments of the invention.

Illustrated in FIG. 10 is the self-assembly of a monomer formed of diketo and diamine units with subsequent metal-catalyzed functionalization based on the basic building unit (I). Using a palladium catalyzed carbonylation reaction, 4 is coupled with commercially available reagent (9) in the presence of CO ((9) may also be synthesized in a one-step, 73% yield reaction). The carbonylation of aryl halides with amines is a routine, industrial scale reaction and thus represents a facile entry into (10). Amides exist as a tautomer with the iminol form (as shown in the boxed inset structures), in which the amide form predominates. However, formation of the imine moiety is easily accomplished as shown using the two-step, one-pot sequence involving palladium-catalyzed reactions. The same reactions employed in the previous materials are applicable here, and alternatives to the use of triflic anhydride are known (such as formation of the imine chlorides via thionyl chloride). Thus, this represents a three-step formation of (11) via a carbonylation, self-assembly upon deprotection of the thiadiazole units (AcOH/Zn) and final analog formation. It should be noted that there are many alternatives to the palladium catalyzed reactions (ether or ester formation). Moreover, the sequence may be modified by Pd-catalyzed functionalization of structure (10) with subsequent self-assembly to produce (11).

Characterization and Applications

Computational studies on inventive OFNMs are predictive of electronic structure as to surface and bulk electrical conduction properties. Commercially available solid-state computational software includes Vienna ab initio simulation package (VASP) and Quantum Espresso (integrated suite of Open-Source computer codes for electronic-structure calculations and materials modeling at the nanoscale that is based on density-functional theory, plane waves, and pseudopotentials) and in particular with the Jambo subroutine In electronic structure calculations, different crystal structures of OFNMs are calculated to predict the relative electronic characteristics of specific structures to guide synthesis and design compositions for specific uses. Such calculations yield total energy and unit cell parameters that can be compared with the X-ray diffraction (XRD) measurements. Electronic structure, density of states, and predictive optical spectrum calculations are also performed to aid in OFNM design and comparison to experimental results obtained from actual material. Conductance and mobility for each 2D OFNM material are also readily calculated for guidance and comparison to experimental data 3D crystals from 2D stacking are also important for ion and charge transfer, optical and magnetic properties. If an inventive OFNM material is used to chelate transition metals within nanopores, the resulting inventive OFNM will have interesting magnetic properties. In addition, the presence of controlled size and electro-affinity nanopores in inventive OFNMs, allows for prediction of proton and ion transfer. Another important feature that can affect the band structure is a pseudo Jahn-Teller distortion that can buckle a flat surface of an inventive 2D OFNM and also change the band structure to remove degeneracies.

The synthesized materials may be characterized by standard techniques. X-ray diffraction provides indications about both the structure and the degree of order in the material. X-ray photoelectron spectroscopy (XPS) and ultraviolet photoelectron spectroscopy (UPS) provide elemental composition, chemical shifts as well valence band structure that can then be compared to theoretical calculations. Solid state NMR probes the chemical environments of H, $C^{13}$ and $N^{15}$ in the structures that also provide information on both how ordered the material is and if edge-terminating groups are present and about the size of ordered domains. SEM with energy-dispersive X-ray spectroscopy (EDX) may be used for routine imaging and spatial analysis of the elemental composition while TEM will directly image the size of the expected 2D flakes and provide lattice images and diffraction from which structural information can be extracted to correlate with the X-ray Diffraction (XRD) I X-ray crystallography to confirm or eliminate various structural possibilities such as stacking polytypes. STM may also be used, since 2D materials are often some of the easiest materials to image, to determine periodic and defect structures and densities of states in both valence and conduction bands. TGA and differential scanning may be used to determine the thermal calorimetry (DSC) stability, phase stability and purity in both air and inert atmospheres. Carrier mobilities may be measured by preparing FET structures and measuring the current voltage behavior as was done for g-$C_2N$ where high mobilities and on/off ratios were measured.

Non-limiting examples of applications of the inventive new materials illustratively include chemically selective membranes, sensors, battery electrodes, heterogeneous catalysis and electrocatalysis, all of which are necessary for improving future energy technologies that will significantly impact society. Furthermore in a fuel cell or electrolyzer application these materials can facilitate gas transport, ion transport, electrical connection, and electrocatalyst binding all in one material. Usually one would need a gas permeable carbon support, an ion conducting polymer (expensive in a PEM), and a particulate electrocatalyst such as Pt. By having a high concentration of bound metals in the macrocycle sites, embodiments of the invention provide excellent catalyst dispersion that may even be achieved using cheaper metals such as Ni with no ripening as with Pt particles.

Chemically selective membranes: The ability to functionalize the nanopores of the graphitic structures allows for designing the nanopores for transporting a specific chemical species. In fuel cells, redox flow batteries, electrolyzers, and desalinization systems the selective transport of ions determines both the efficiency and cost of these devices. The special ability of NAFION® and related proton transport membranes is required in most advanced fuels cells, however the cost of this fluorocarbon polymer is now a major factor in the overall cost of these devices. In addition an OFNM replacement will be more thermally stable than Nafion® that loses its specificity at higher temperatures limiting its performance. Since both the size and the chemical composition of the nanopores of the proposed graphitic structures can be rationally modified there is an ability to prepare membranes that are specific to a particular ion. For example, the nanopores may be functionalized with negatively charged sulfonate groups, as in Nafion®, to be proton specific if the pore is small or specific for larger cations if the pore is larger. Functionalizing the nanopores with protonated ammonium cationic groups results in charge and/or size selective transport of anions that is needed for the next generation of redox flow batteries since the crossover of transition metal cations, the preferred redox couples in these batteries, is one of the primary issues in improving their efficiency and cycle life. Ion transport measurements have been made on both single layer and composite membranes made from these materials. The single layer transport measurements have been made using methods that have been developed to resolve the controversy of whether graphene itself was a proton specific membrane. To determine that proton transport through single sheets of graphene was due to defects rather than proton tunneling, Keyser et al. (Appl. Phys. Lett. 107, 213104 (2015); http://dx.doi.org/10.1063/1.4936335) have isolated tiny, single sheets of graphene on the opening of a pulled pipette tip. Ion currents can then be measured by placing electrodes inside and outside the pipette while immersed in an electrolyte. Either an applied potential or a chemical potential difference between the inside and the outside of the pipette allows for the measurement of ion flow across the membrane. Composite membranes have also been made and evaluated. When selective ion transport of a cation and anion occurs, a bipolar membrane may then be constructed by layering the two 2D materials. Since the membrane materials themselves are semiconducting, application of a potential to the two sides of the membrane, to drive the respective semiconductors into accumulation, would also remove the need for the external anode and cathode usually needed in bipolar membrane devices. Calculations may be performed to predict which ions will be selected in each type of the functionalized pores, and how well they will move in the nanopores and these calculations will then be compared with experimental results.

Figure 11:
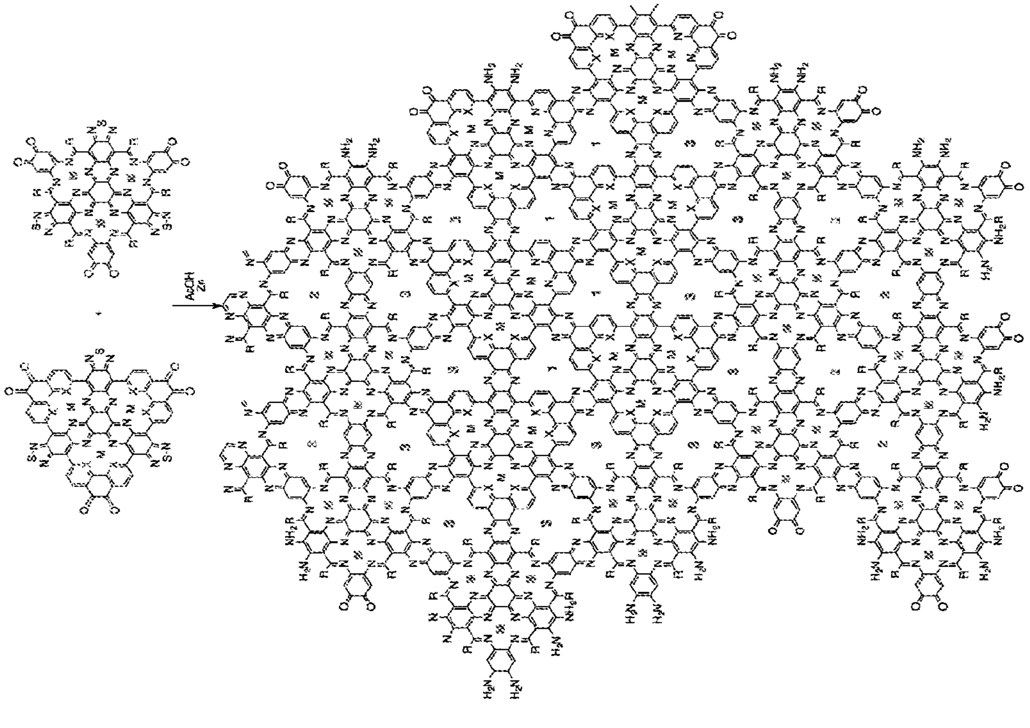
FIG. 11 illustrates the formation of three, four, and five hole nanopore systems in accordance with embodiments of the invention.

Formation of Three, Four, and Five Hole-Nanopore Materials:

In specific inventive embodiments variations of the two-nanopore system embodiments shown in FIG. 9 and FIG. 10 may be used to build 3-5 nanopore materials by using a combination of the two building blocks as shown in FIG. 11. The differences/variations of the starting materials are highlighted in red for each. M (Metals) are placed in each pore to help differentiate them in the final material. The reaction shown in FIG. 11 is based on the reaction of one building block, M, followed by the addition and reaction of the second building block, M'. The reaction shown produces holes 1 and 2 and a new hole, 3, which would be formed at the interface. Five holes are produced if no metals are incorporated in the starting material, 4 holes if only one starting material incorporates a metal, and 3 holes if metals are inserted in both starting materials prior to reaction. There are several variations on this theme; such as ordered addition or just random if both materials are added at once, and the like.

Additional Embodiments

Figure 13A:
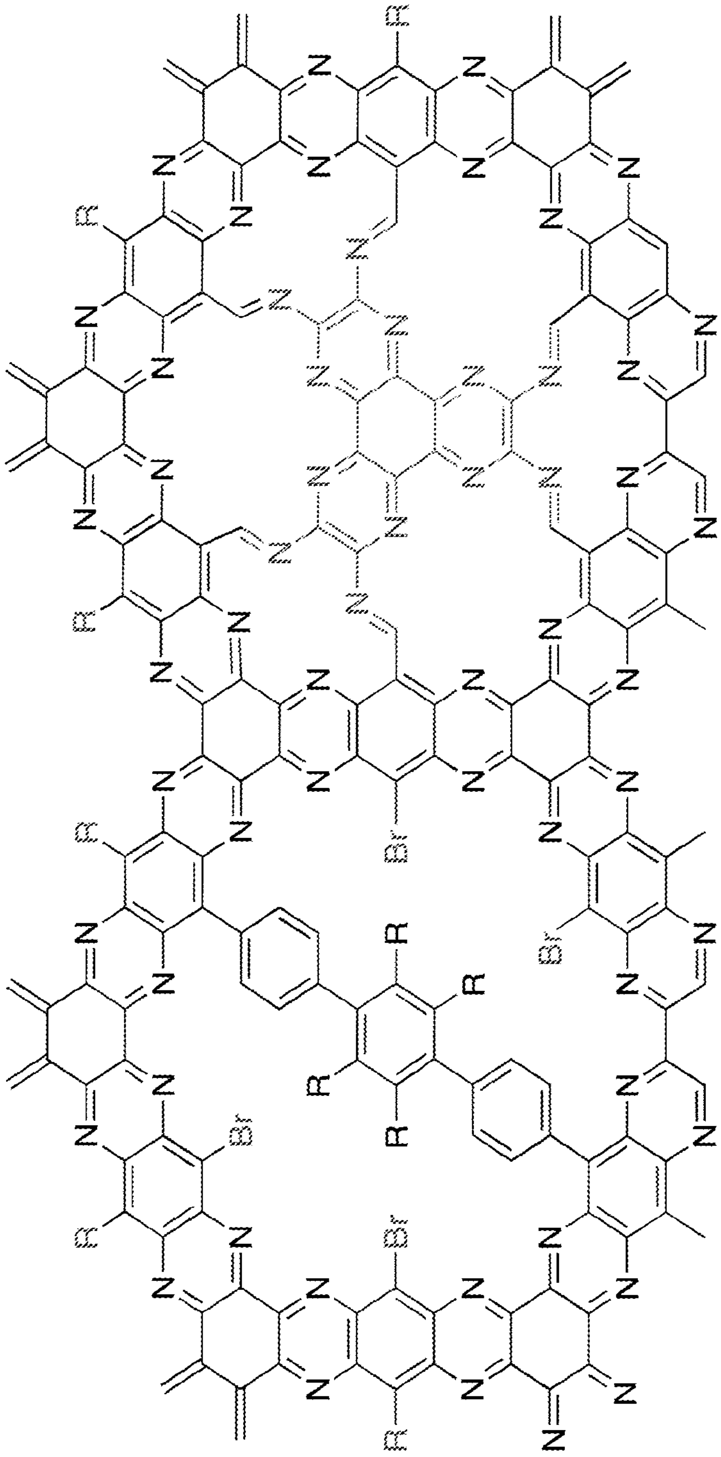
FIGS. 13A and 13B illustrate R groups for incorporation into OFNMs in accordance with embodiments of the invention.
Figure 13B:
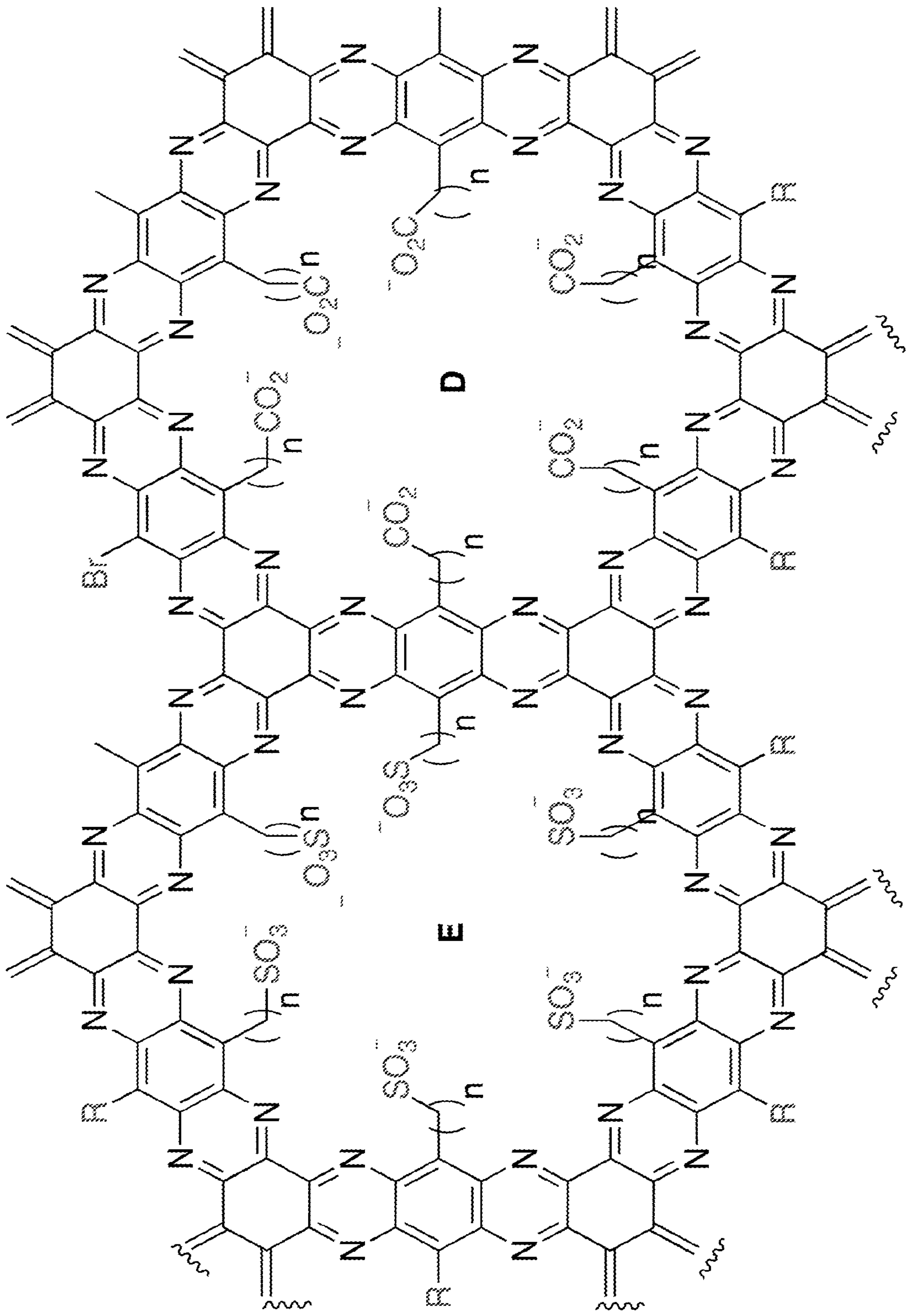

FIGS. 13A and 13B illustrate R groups for incorporation into OFNMs illustratively including: hydrogen, sulfur states (i.e., sulfonate, thiols, etc.), nitrogen—1°, 2°, 3°, 4° and ammonium, halide—(F, Cl, Br & I); carboxylic acid derivatives—carboxylic acids, carboxylate, esters and amides, acetylenes—terminal and internal, aromatic rings including heteroaromatics; and biomolecules: amino acids derivatives (peptides, proteins & enzymes) and carbohydrates. In addition, nanopore bridging groups such as triphenyl (below left in FIG. 13A) would also incorporate R groups on the bridging group and other bridging groups to form second holes (below right in FIG. 13A). FIG. 13B illustrates alkanes and alkane extensions, in which n=0-3 to modify the nanopore size.

Figure 14A:
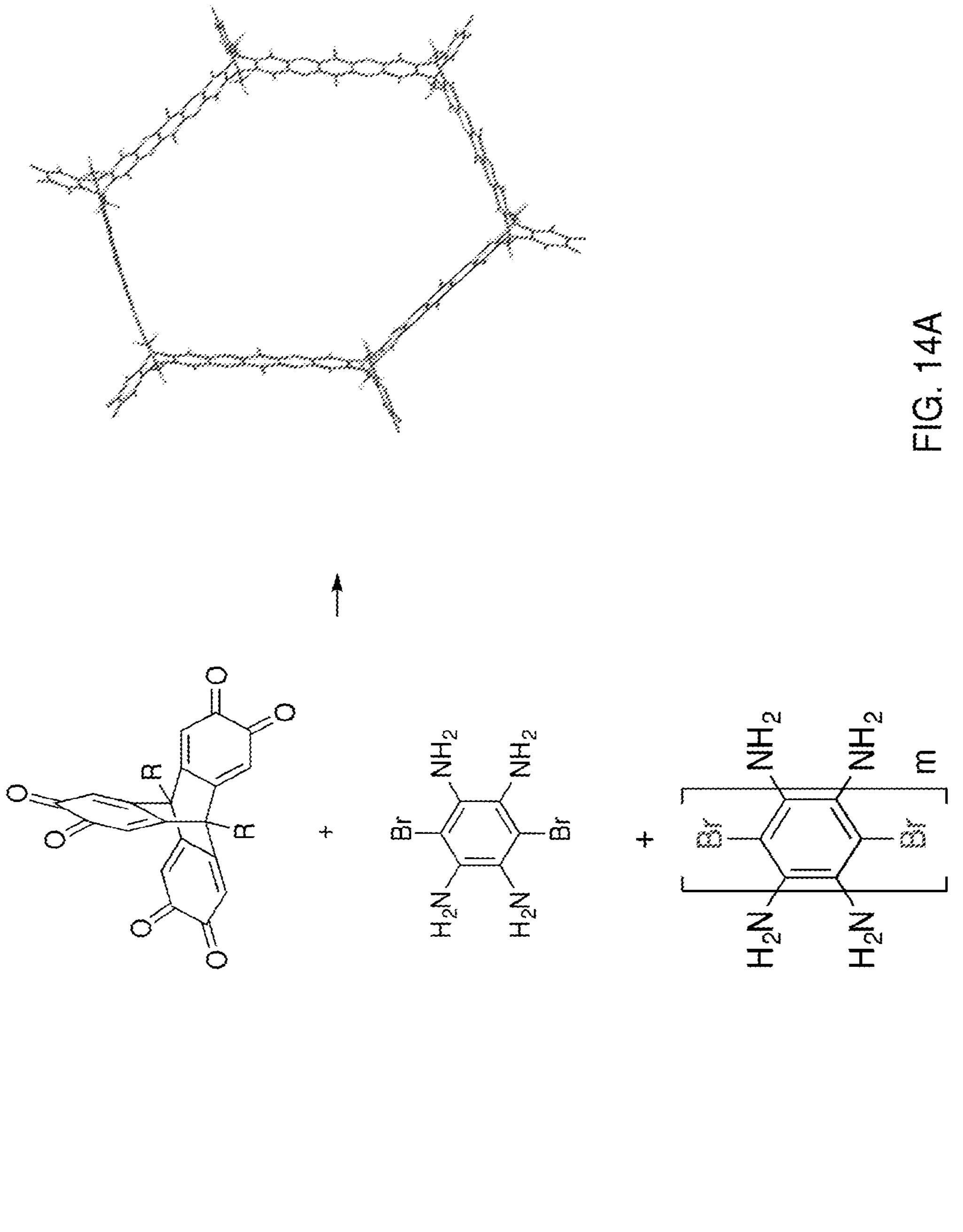
FIGS. 14A-14D illustrate the formation of scaffolds in accordance with embodiments of the invention.
Figure 14B:
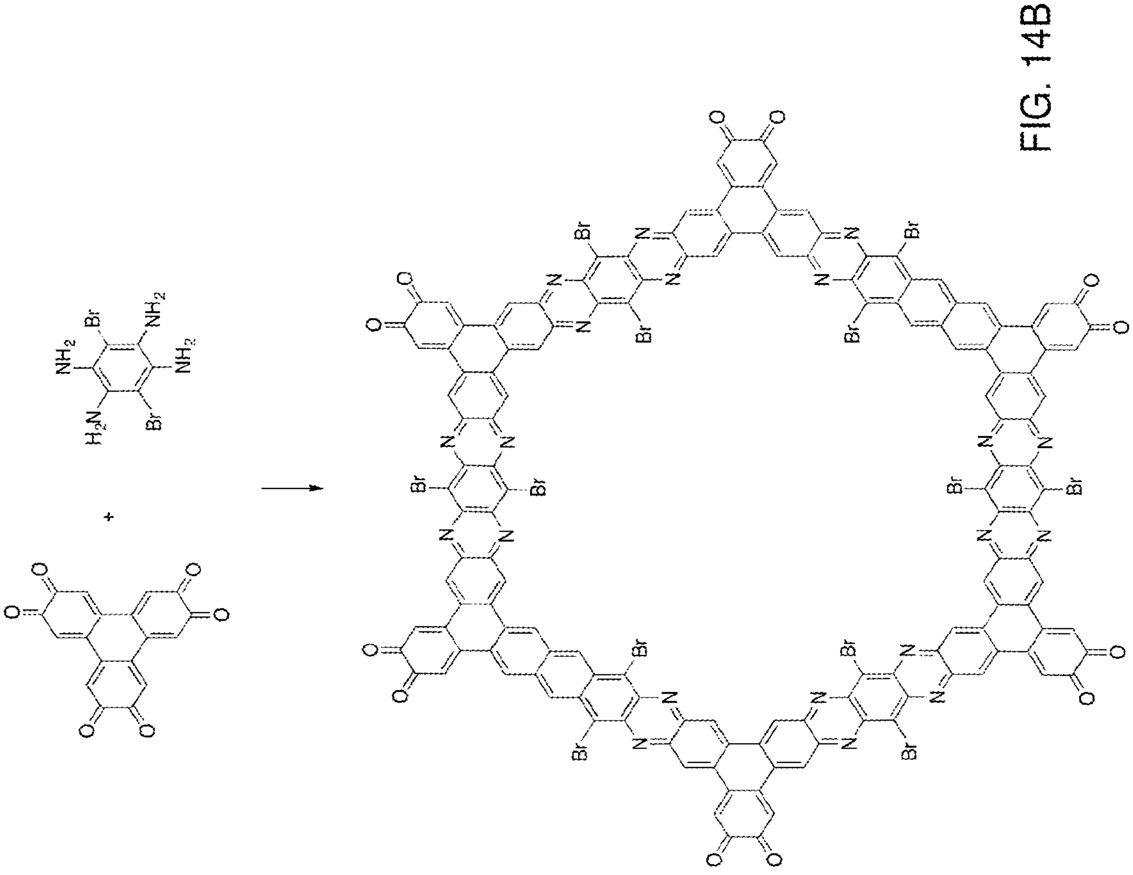
Figure 14C:
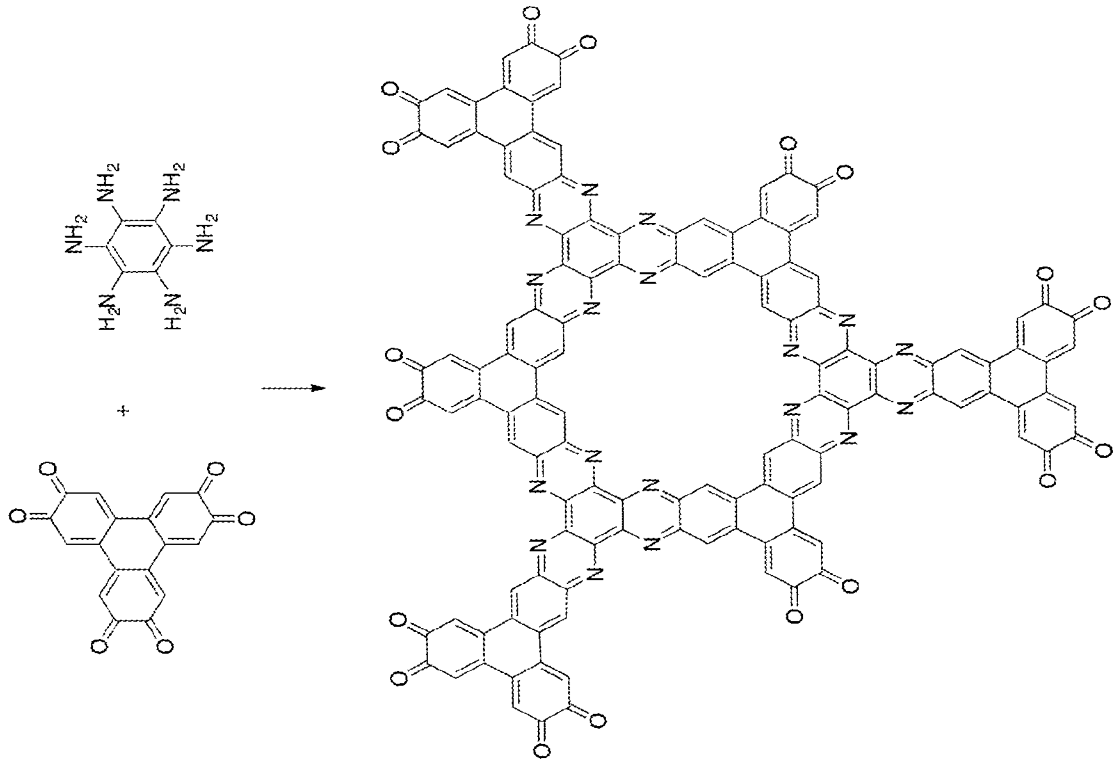
Figure 14D:
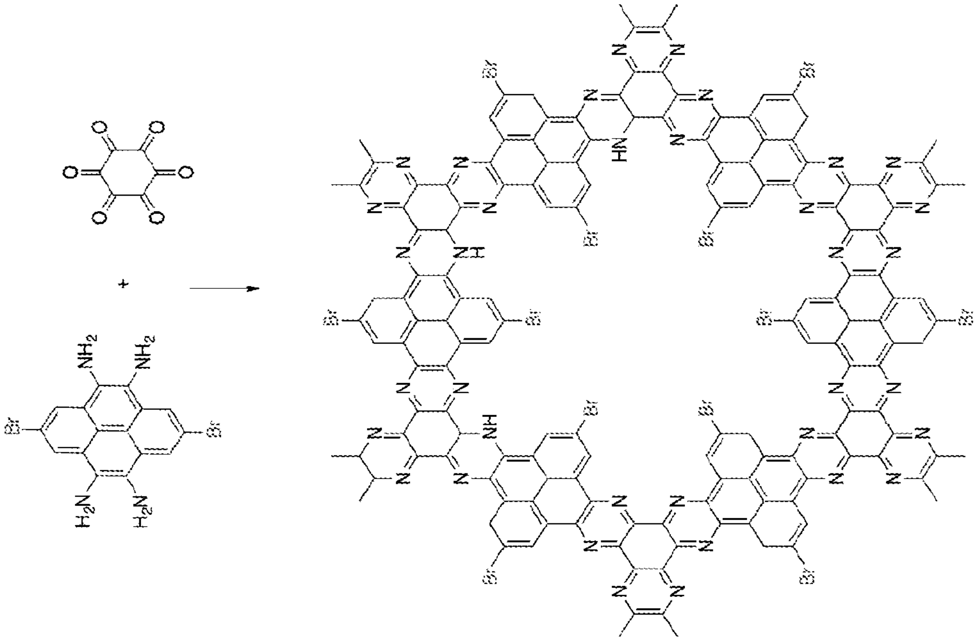

FIGS. 14A-14D illustrate the formation of scaffolds. FIG. 14A illustrates triptycene and naphthalene derivatives, where the triptycene OFNM is depicted as a single pore in the upper portion of FIG. 14A, and the napthalene derivatives are shown at the bottom of FIG. 14A. FIG. 14B illustrates a triphenylene hexaone, and more specifically a triphenylene-2,3,6,7,10,11-hexaone derived OFNM depicted as a single pore. FIG. 14C illustrates a triphenylene hexamine, and more specifically a triphenylene-2,3,6,7,10,11-hexaone with a hexaaminobenzene derived OFNM depicted as a single pore. FIG. 14D illustrates a 4,5,9,10-tetramine pyrene, and more specifically 4,5,9,10-tetramine pyrene with hexaketocyclohexone derived OFNM depicted as a single pore.

References cited herein are indicative of the level of skill in the art and are incorporated by reference to the same extent as if each reference was individually and explicitly incorporated by reference.

The foregoing description is illustrative of particular embodiments of the invention, but is not meant to be a limitation upon the practice thereof. The following claims, including all equivalents thereof, are intended to define the scope of the invention.

The invention claimed is:

1. An ordered functional nanoporous material (OFNM) composition having at least one nanopore comprising:

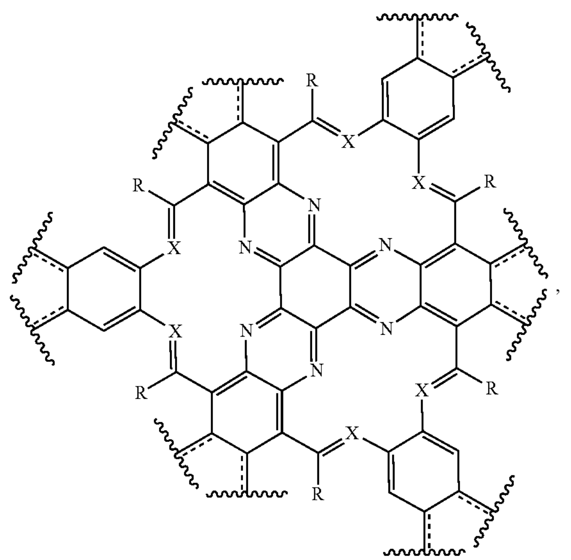

, wherein:

X is N or CH;

dashed bonds (---) indicate that the bond is a single bond or a double bond;

each R is independently H, Cl, Br, I, $C_4H_4S$, $SO_3H$, $CO_2H$, C≡CH, CH═$CH_2$, $NH_3$, OH, C≡N, $C_1$-$C_4$ alkyl, $(CH_2)_x$CH═$CH_2$, or $(CH_2)_y$CH═CH$(CH_2)_z$ where x or (y+z) is an integer of 0 to 4 inclusive, $(CH_2)_j$CH≡CH, or $(CH_2)_k$CH≡C$(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, SH, primary amine, secondary amine, tertiary amine, OH, $CO_2H$, $SO_3H$, or $C_2$-$C_4$ alkenyl; and partial bonds (∿) are completed by joining to complementary portions of other nanopores or are a terminal substituent comprising $NH_2$ or O.

2. The OFNM composition of claim 1, wherein X in at least one occurrence is N.

3. The OFNM composition of claim 1, wherein R in every occurrence is at least one of Cl, Br, I, $C_4H_4S$, $SO_3H$, $CO_2H$, C≡CH, CH≡$CH_2$, $NH_3$, OH, C≡N, $C_1$-$C_4$ alkyl, $(CH_2)_x$CH≡$CH_2$, or $(CH_2)_y$CH≡CH$(CH_2)_z$ where x or (y+z) is an integer of 0 to 4 inclusive, $(CH_2)_j$CH≡CH, or $(CH_2)_k$CH≡C$(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, SH, primary amine, secondary amine, tertiary amine, OH, $CO_2H$, $SO_3H$, or $C_2$-$C_4$ alkenyl.

4. The OFNM composition of claim 1, wherein R in at least one occurrence is $C_1$-$C_4$ alkyl in which a hydrogen is substituted with halide, SH, OH, $CO_2H$, or $SO_3H$.

5. An ordered functional nanoporous material (OFNM) composition having at least one nanopore comprising:

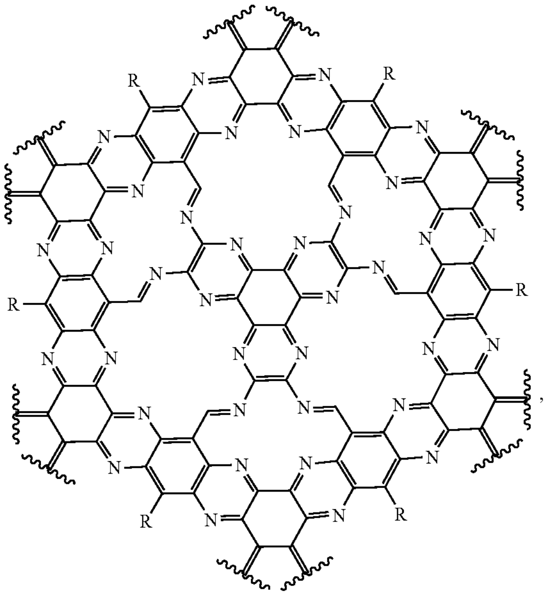

, wherein:

each R is independently H, Cl, Br, I, $C_4H_4S$, $SO_3H$, $CO_2H$, C≡CH, CH═$CH_2$, $NH_3$, OH, C≡N, $C_1$-$C_4$ alkyl, $(CH_2)_x$CH≡$CH_2$, or $(CH_2)_y$CH═CH$(CH_2)$ z where x or (y+z) is an integer of 0 to 4 inclusive, $(CH_2)_j$CH≡CH, or $(CH_2)_k$CH≡C$(CH_2)$ r where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, SH, primary amine, secondary amine, tertiary amine, OH, $CO_2H$, $SO_3H$, or $C_2$-$C_4$ alkenyl; and partial bonds (~) are completed by joining to complementary portions of other nanopores.

6. The OFNM composition of claim 5, wherein R in at least one occurrence is $C_4H_4S$, $SO_3H$, $CO_2H$, C≡CH, CH═$CH_2$, $NH_3$, OH, C≡N, $C_1$-$C_4$ alkyl, $(CH_2)_x$CH≡$CH_2$, or $(CH_2)_y$CH≡CH$(CH_2)_z$ where x or (y+z) is an integer of 0 to 4 inclusive, $(CH_2)_j$CH≡CH, or $(CH_2)_k$CH≡C$(CH_2)_r$ where j or (k+r) is an integer of 0 to 4 inclusive, an aromatic, a heteroaromatic, an amino acid, a glycol, a sugar, a dipeptide, a tripeptide, an oligopeptide, a protein, a nucleic acid, a virus, or a substituted form of any of the aforementioned in which an aliphatic or aromatic hydrogen is replaced with a substituent of a halide, SH, primary amine, secondary amine, tertiary amine, OH, $CO_2H$, $SO_3H$, or $C_2$-$C_4$ alkenyl.

7. The OFNM composition of claim 5, wherein R in at least one occurrence is $C_1$-$C_4$ alkyl in which a hydrogen is substituted with halide, SH, OH, $CO_2H$, or $SO_3H$.

8. The OFNM composition of claim 5, wherein R in at least one occurrence is $C_1$-$C_4$ alkyl in which a hydrogen is substituted with $CO_2H$ or $SO_3H$.

* * * * *